United States Patent [19]

Odell et al.

[11] Patent Number: 5,662,617
[45] Date of Patent: Sep. 2, 1997

[54] MANUALLY PIVOTED BARRIER ASSEMBLY FOR PIERCING ELEMENT

[75] Inventors: Robert B. Odell, Franklin Lakes; Sandor Szabo, West Orange; James A. Burns, Elizabeth, all of N.J.

[73] Assignee: Becton, Dickinson and Company, Franklin Lakes, N.J.

[21] Appl. No.: 597,329

[22] Filed: Feb. 6, 1996

Related U.S. Application Data

[63] Continuation of Ser. No. 375,841, Jan. 20, 1995, abandoned, which is a continuation-in-part of Ser. No. 310,538, Sep. 23, 1994.

[51] Int. Cl.$^6$ ................................................. A01M 5/32
[52] U.S. Cl. ........................ 604/192; 604/263; 128/919
[58] Field of Search ............................ 604/192–198, 604/110, 187, 263; 128/919

[56] References Cited

U.S. PATENT DOCUMENTS

| | | | |
|---|---|---|---|
| 4,659,330 | 4/1987 | Nelson et al. | 604/192 |
| 4,664,259 | 5/1987 | Landis | 206/365 |
| 4,982,842 | 1/1991 | Hollister | 206/365 |
| 5,011,475 | 4/1991 | Olson | 604/192 |
| 5,055,102 | 10/1991 | Sitnik | 604/192 |
| 5,135,509 | 8/1992 | Olliffe | 604/192 |
| 5,151,089 | 9/1992 | Kirk, III et al. | 604/192 |
| 5,154,285 | 10/1992 | Hollister | 206/365 |
| 5,188,611 | 2/1993 | Orgain | 604/192 |
| 5,207,653 | 5/1993 | Janjua et al. | 604/192 |
| 5,242,417 | 9/1993 | Paudler | 604/192 |
| 5,312,369 | 5/1994 | Arcusin et al. | 604/192 |
| 5,509,907 | 4/1996 | Bevilacqua | 604/263 |
| 5,584,816 | 12/1996 | Gyure et al. | 604/192 |

FOREIGN PATENT DOCUMENTS

| | | |
|---|---|---|
| 0 460 914 A1 | 4/1991 | European Pat. Off. . |
| 3713754A1 | 4/1987 | Germany . |
| 1 233 302 | 7/1969 | United Kingdom . |
| 2277 685 | 11/1994 | United Kingdom . |
| WO93/16745 | 2/1993 | WIPO . |
| WO93/23312 | 11/1993 | WIPO . |

*Primary Examiner*—Corrine M. McDermott
*Assistant Examiner*—V. Alexander
*Attorney, Agent, or Firm*—Vincent A. Castiglione

[57] ABSTRACT

A protective barrier assembly for shielding a piercing element such as a pointed needle cannula or blunt ended cannula during or after use of a medical implement. The piercing element includes a longitudinal axis, a length, a distal end which may be pointed or blunt, a proximal end and a passageway therethrough. The assembly may include a hub configured for mounting to a medical implement such as a syringe or evacuated tube holder and having an axial opening through it for receiving the needle so that the distal end of the needle projects outwardly. The assembly also includes a shield with an open end, a closed end, and a sidewall portion with a longitudinal slot extending from the open end toward the closed end. The shield has a first position exposing the needle and a second position wherein the shield obstructs unintentional access to the needle. The shield may be mounted to the hub by a hinge opposite the slot, so that when the slot is moved from the first position to the second position, the slot provides clearance for the needle. A retaining and/or locking mechanism may be incorporated as part of the shield or made integral with the hinge so as to retain/lock the shield in the second position.

14 Claims, 29 Drawing Sheets

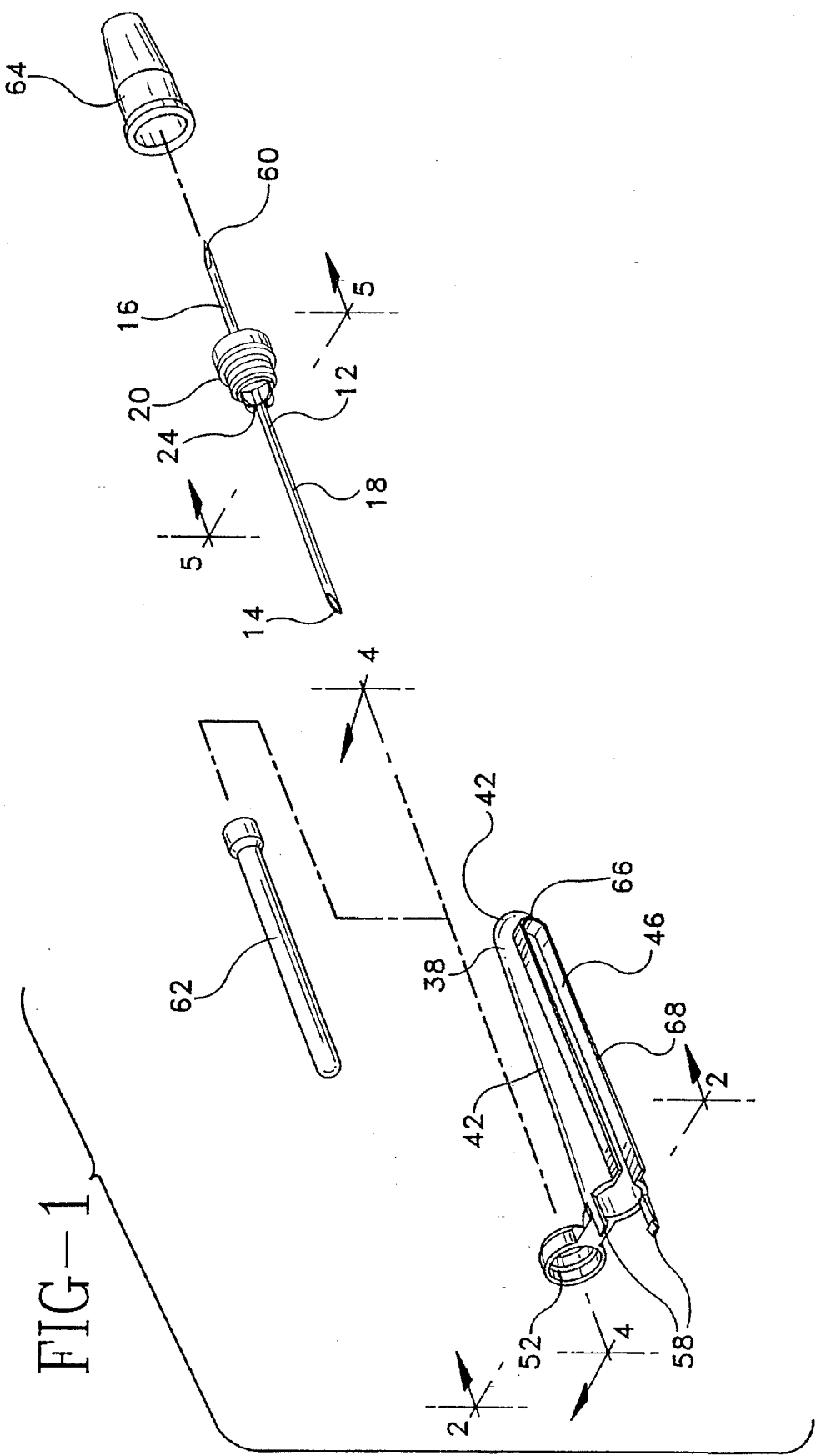

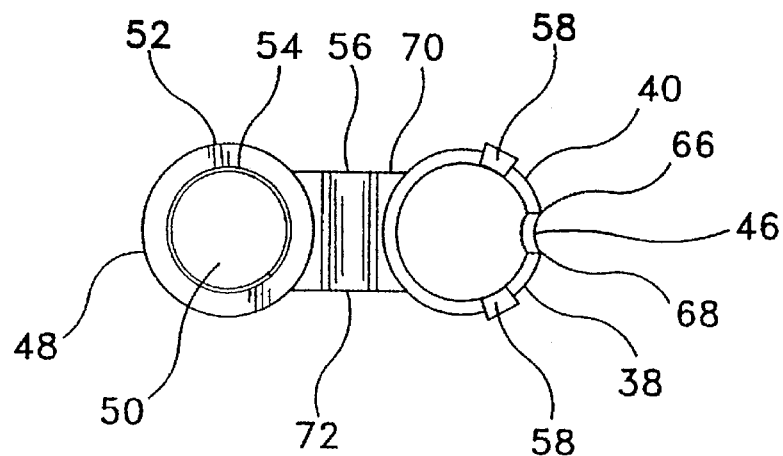
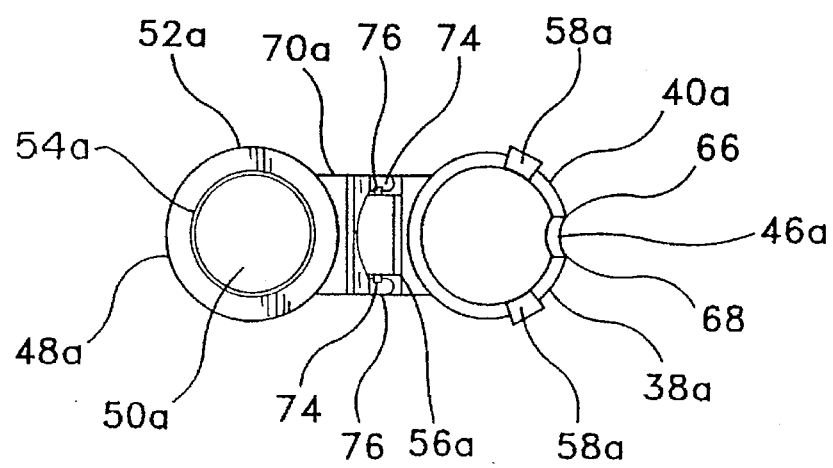

MANUALLY PIVOTED BARRIER ASSEMBLY FOR PIERCING ELEMENT

I. CROSS REFERENCE TO RELATED APPLICATIONS

This application is a continuation of application Ser. No. 08/375,841, filed Jan. 20, 1995 now abandoned, which is a continuation-in-part of applicants' application Ser. No. 08/310,538, filed Sep. 23, 1994, now pending.

II. FIELD OF THE INVENTION

The present invention relates to a barrier assembly for a piercing element, and more particularly, the invention relates to a manually pivotable barrier assembly for protectively covering the distal tip of a piercing element during interim use or subsequent to completion of use of the piercing element.

III. BACKGROUND

There has been a marked increase in the use of disposable medical implements, particularly medical delivery or collection implements, such as hypodermic needles/syringes or evacuated blood collection tubes. Typically, such medical implements include piercing elements for administering a medication or withdrawing a fluid. Such piercing elements include, inter alia, pointed needle cannulae or blunt ended cannulae.

Exposure to blood borne pathogens is a recognized hazard by anyone associated with the medical arts. As a result of this recognition, numerous protocols for the use of piercing elements such as needles have been developed and are practiced. The problem of transmission of blood borne pathogens not only exists for the physician, nurse or phlebotomist using the needles, but also for support workers all through the hospital. Since most needles in use today are single-use and disposable, hospital service personnel are at risk from needles that are not properly handled by the users. A definite need has developed for ways to safely and conveniently handle and transport such implements, both during interim use of the implement and after use is completed, so that disposal can be effected while reducing the risk of exposing any person handling the used implements to injury, infection or disease by puncture or contact with a used needle.

In today's medical facilities, then, a wide variety of disposable needle devices are routinely used to administer medication by injection and intravenous ("I.V.") procedures, or for intravenous collection or withdrawal procedures such as blood collection. Either interim the completion of a procedure or once an injection is given, a blood sample dram, or an I.V. needle removed from a patient, both the needle and/or syringe or tube used in the procedure may be contaminated and must be either handled or disposed of in a safe manner. The problem is particularly heightened because competent medical personnel will not normally leave a patient unattended immediately after administering an I.V. procedure in order to search out disposal facilities for the used medical implement. Consequently, while the nurse or physician is attending to the patient, unsheathed contaminated needles have been momentarily placed on bedside tables, the used needles have been placed on the patient's bedding, and bed mattresses have even been used as a type of "pincushion" to temporarily hold the contaminated needle.

The needle use protocols previously mentioned generally dictate in detail when and how a needle will be used and how it should be disposed of. The problem with many protocols for handling needles is that the protocols often require users to perform additional steps in a procedure. With the pressure of time and simple carelessness, certain practices regarding handling of used needles are sometimes disregarded and injuries may occur.

For instance, it has been a practice to break or cut a piercing element such as a needle after use and before transport to ultimate disposal so as to eliminate the sharp end point, thereby reducing the risk of puncture, scratching or other injury which might result from handling. However, the very act of breaking or cutting the needles may expose the medical personnel to accidental puncture during the breaking or cutting operations. In addition, residual medication or blood in the needle or the syringe can splatter onto the person or his clothes, and potentially harmful fumes from the residual medication could be inhaled as a result of the so-called aerosol effect. Furthermore, the blades of the cutting tool might possibly serve as a breeding ground for germs, bacteria and other disease-causing micro-organisms to which an unsuspecting person cutting the needle could be unnecessarily exposed. Recently, an even greater danger has been recognized in connection with the handling and disposal of used needles as well as other sharp medical implements. It is now believed that certain diseases, most notably Hepatitis B, can be transmitted by covert percutaneous—i.e., by merely contacting the contaminated needle or implement.

While the used needle portion of a needle/medical implement combination presents the most significant risk of injury or injection through accidental puncture or scratching of a person's skin, the used implement part may also present a risk of infection. For example, a used implement such as a syringe, a blood collection shield, or the like can contain residual blood or medication which, if exposed to a person's skin, may be absorbed topically (particularly if a cut or break in the skin is present) and may cause a serious internal infection or other reaction. As a result of the foregoing dangers, it is preferred current practice to dispose of such devices intact, without dismantling them.

One contemplated solution lies in disposing of the whole, used piercing element/implement by recapping it before disposal with its original, protective sheath. The contaminated needle point and shaft would thus be isolated against inadvertent contact or puncture until it could be deposited in a disposal unit. Previously, the recapping solution was discouraged because of the inherent risk of accidental puncture if the person was unsuccessful in re-inserting the needle into the sheath. While the U.S. Occupational Safety and Health Administration ("OSHA") has stated that needle recapping is permissible so long as some type of recapping device is utilized to aid in the recapping procedure, it is apparent that attempts by medical personnel to recap a used piercing element sometimes carries the risk of inadvertent puncture or touch contact, owing in great part to the exigencies and great stresses of the working environments in which practitioners use the devices.

One proposal for a recapping device requires the device to be held in one hand (with the sheath held in the device) while the needle is held in the other hand for insertion into the sheath. While such a device may be effective in reducing the risk of accidental needle sticks, it suffers a significant drawback because it requires two hands to use. Once a user picks up the handle portion with one hand, the handle is unsterile by any contaminant on the user's hand. When someone else picks up the device, his/her hand is immediately contaminated by any residue from the previous user's hand.

The medical device industry has further responded to the problem by producing a wide variety of sharps collectors, needle shielding devices and the like to assist practitioners in their need to reduce the occurrence of needle injuries. Many devices have also been developed for shielding needles after use to avoid exposing other workers to used needles. A representative listing of many of these devices is found in U.S. Pat. No. 4,982,842 to Hollister et al. Hollister et al. lists 90 U.S. patents of various devices for guarding a needle as part of the background for the present shielded needle container. Hollister et al. discloses a stand alone adapter that has a male and female end for mating with a needle assembly and the ejection end of a syringe. The device of Hollister et al. includes a housing mounted to the adapter which may be pivoted to a position in alignment with the needle for enveloping the needle and locking the needle to retain it in the housing. The Hollister et al. device increases the unusable or "dead" volume of the device on which the adapter is mounted, requires an additional part which increases the projection of the needle hub, and the mechanism for holding the cap onto the needle snaps onto the needle itself, which may create an aerosol of any fluid remaining on the needle. Also, if bevel position is important to the intended use of the needle, the Hollister et al. invention must be carefully aligned with the needle point when mounted.

U.S. Pat. No. 5,207,653 to Janjua et al. discloses a needle cap with a longitudinal slit having a width greater than the width of a needle. According to Janjua et al., the needle cap is adapted to be pivotally connected with the needle and hub piece. Janjua et al. also discloses that the needle cap is usable with a syringe or with a needle holder for fluid collection tubes. The device disclosed by Janjua et al. mounts on the needle hub with a pivot, but since it only pivots in one plane, unless the needle point is precisely with the hub oriented during assembly, the shield may interfere in some applications.

Many of the devices listed in the background of the Hollister et al. patent, the Hollister et al. invention itself and the Janjua et al. invention all attempt to address the recognized need to protect medical and service personnel from needle sticks. There are several recurrent problems in varying degrees with all these devices. Many of the devices are somewhat complex, hence are significantly more costly than an unprotected device. Many of the devices increase the complexity or increase the difficulty of performing a procedure. Some devices are so specific that they preclude use of the device in certain procedures. For these and similar reasons most of the devices in the Hollister et al. background have never been successfully commercialized.

Blood drawing is one application that is particularly sensitive to needle point orientation. Most phlebotomists carefully align a needle point with the beveled face away from the skin so that the needle point placement may be precisely controlled. A needle assembly as disclosed in Janjua et al. would either sometimes be clumsy to use because the shield would sometimes be in the way or, alternatively, more expensive because of the need to carefully orient the point during manufacture. Additionally, in Janjua et al., while there is a recognition of the need to secure the cap in the closed position over the needle, all of the solutions proposed require additional steps such as securing the cap with an adhesive or twisting the cap.

There is a need, therefore, for a way to protect a used piercing element from inadvertent touch contact and to provide a safe, reliable way to dispose of the used piercing element so as to address the problems noted hereinabove.

Although there already are many shielded needle devices, there is still a need for a shielded needle device that is easily manufactured, applicable to many devices and simple to use. Additionally, the needle device should not interfere with normal practices of use.

IV. SUMMARY OF THE INVENTION

The above voiced concerns are addressed by a shielded needle assembly in accordance with the invention. The needle assembly includes an elongate piercing element such as a pointed needle cannula or a blunt ended cannula with a passageway or lumen extending therethrough. The assembly preferably includes a hub having a proximal end, a distal end and an outside surface. The hub may feature an axial opening therethrough for receiving the needle so that the distal end of the needle projects outwardly. The hub may further include elements for releasably mounting the hub onto a fluid handling device such as a hypodermic syringe or an evacuated blood collection tube.

The assembly may further include a shield with an open end, a closed end and an enclosing sidewall portion with a slot extending from the open end toward the closed end. The shield has a first position wherein the piercing element is exposed for use and a second position where the shield substantially encloses the piercing element therein to prevent inadvertent touch contact with the piercing element and particularly obstructs access to the tip of the piercing element.

A mounting collar is provided to secure the shield to the hub. The collar can be formed separate from the hub, or it can be made integral with the hub. In one version, the mounting collar may be rotatable about the hub. A hinge may also be attached at or near the open end of the shield opposite to the slot, and can be formed as part of the mounting collar. The slot is preferably formed sufficiently large enough to provide a clearance for the piercing element, thereby allowing the shield to pivot on the hinge from the first position to the second position.

Numerous closing and/or locking assemblies may be provided to releasably retain the shield in the second position during interim use of the implement, as well as to lockably retain the shield in the second position after full use of the implement for safe disposal. In one embodiment, the open end of the shield may include at least one element to lock the shield in the second position. The locking assembly may be incorporated as part of the hinge or it can be associated with other components of the assembly.

In a preferred embodiment, the piercing element projects proximally outwardly from the hub and includes a proximal point for penetrating a stopper of a fluid collection tube. The piercing element can be formed separate from the medical delivery instrument (such as a syringe) or it can be an integral component of the medical delivery device. In this embodiment, the elements for releasably mounting the hub preferably include a proximal thread for mounting the hub onto a tube holder. Alternatively, in another preferred embodiment, the element for releasably mounting the hub may be configured to retain the hub onto a medical delivery or collection device such as a hypodermic syringe.

The needle assembly of the present invention is simple to manufacture. Since it may be rotatably mounted on the hub, no requirement to orient the point is imposed on the manufacturing process. The needle shield can be easily rotated out of the way when the needle is in use, and is easily moved to the closed position substantially preventing inadvertent access to the needle. The needle shield locks in the closed position without requiring any additional action by the user.

V. BRIEF DESCRIPTION OF THE DRAWINGS

The invention will now be described in greater detail by way of reference to the appended drawings, wherein:

FIG. 1 is an exploded perspective view of a preferred embodiment of the present invention;

FIG. 2 is a sectional view along the line 2,2 of the shield and mounting portion of the embodiment of FIG.1;

FIG. 3 is a sectional view, similar to the view of FIG. 2, illustrating an alternate embodiment of the hinge;

DETAILED DESCRIPTION OF THE INVENTION

Figure 4:
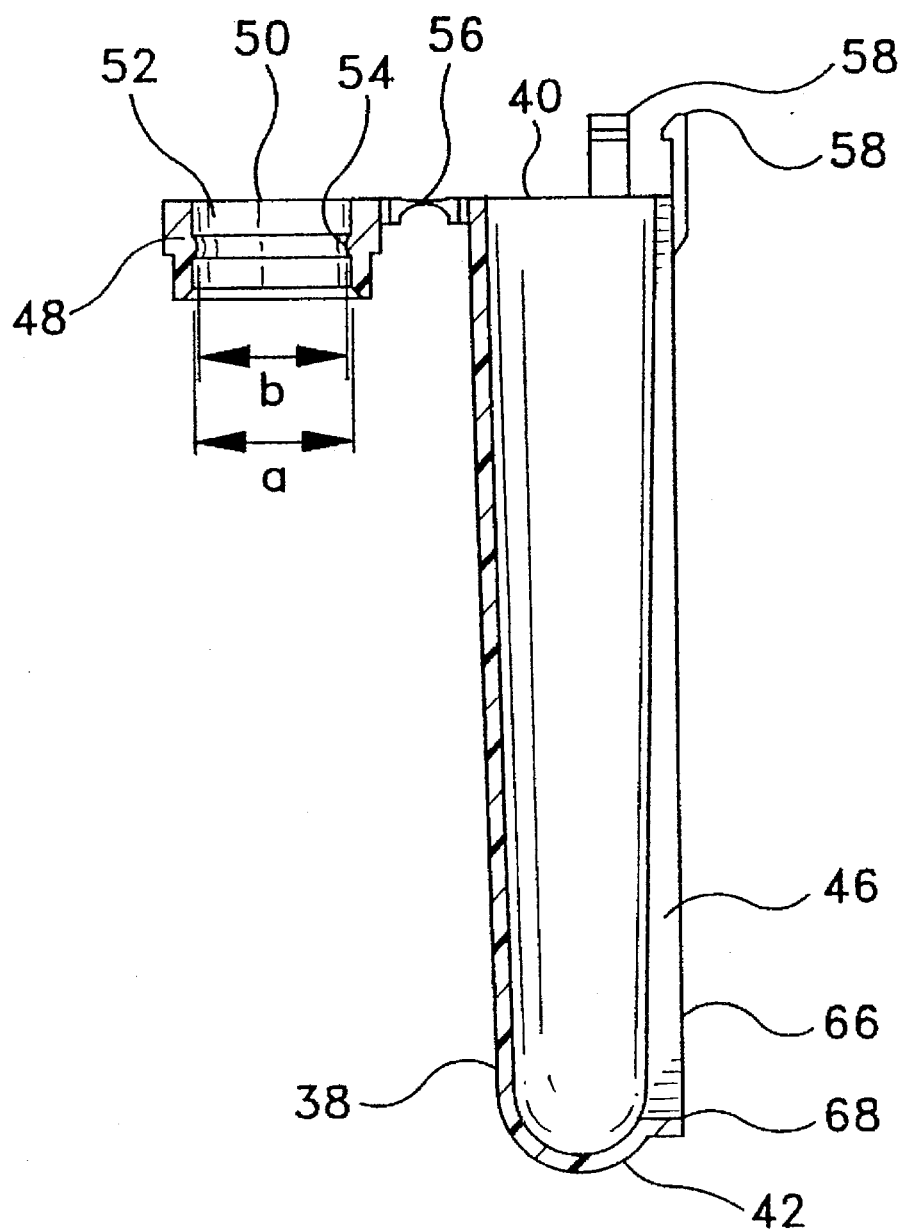
FIG. 4 is a cross sectional view of the shield and mounting portion of the embodiment of FIG. 1 along the line 4,4.
Figure 5:
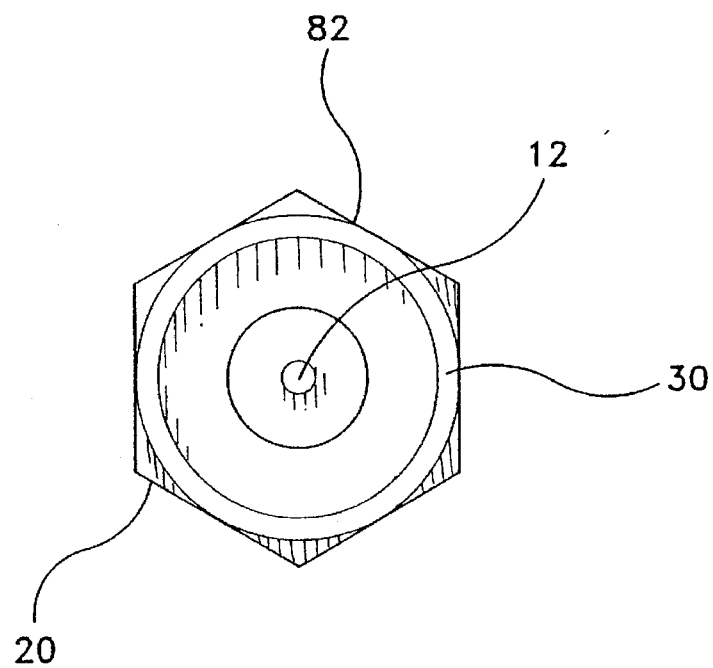
FIG. 5 is a sectional view along the line 5,5 of the hub portion of the embodiment of FIG. 1.

While this invention is satisfied by embodiments in many different forms, there is shown in the drawings and will herein be described in detail, several embodiments of the invention with the understanding that the present disclosure is to be considered as exemplary of the principles of the present invention and is not intended to limit the scope of the invention to the embodiments illustrated. The scope of the invention will be measured by the appended claims and their equivalents.

A convention adopted for this disclosure is that the term "distal" refers to the direction away from a user of the invention and the term "proximal" refers to the direction toward the user.

Additionally, as used throughout this disclosure, the term "piercing element" is intended to encompass the broad range of penetration fluid delivery elements known in the art, inclusive of pointed or sharpened needle cannulae as well as blunt ended cannulae. It will also include cannulae supplied separately from and thereafter attached to the medical delivery instrument, as well as cannulae formed with during manufacture or otherwise considered integral with the medical delivery instrument. For ease of understanding but not of limitation, the term "needle" is used interchangeably with the term "piercing element" in the description, solely to facilitate the reader's understanding and appreciation of the invention, and without intent to limit the scope of the invention to piercing elements formed as sharpened needles.

Referring then to FIGS. 1 to 7, a protective barrier assembly or shielded needle assembly 10 of the present invention includes a piercing element such as a needle 12 having a longitudinal axis X, a pointed distal end 14, a proximal end 16 and a passageway 18 therethrough. One preferred assembly includes a hub 20 having a longitudinal axis X', a proximal end 22, a distal end 23 and an outside surface 26 having an outside diameter "a." Hub 20 preferably has an opening 24 for receiving needle 12 so that distal end 14 projects outwardly.

Figure 11:
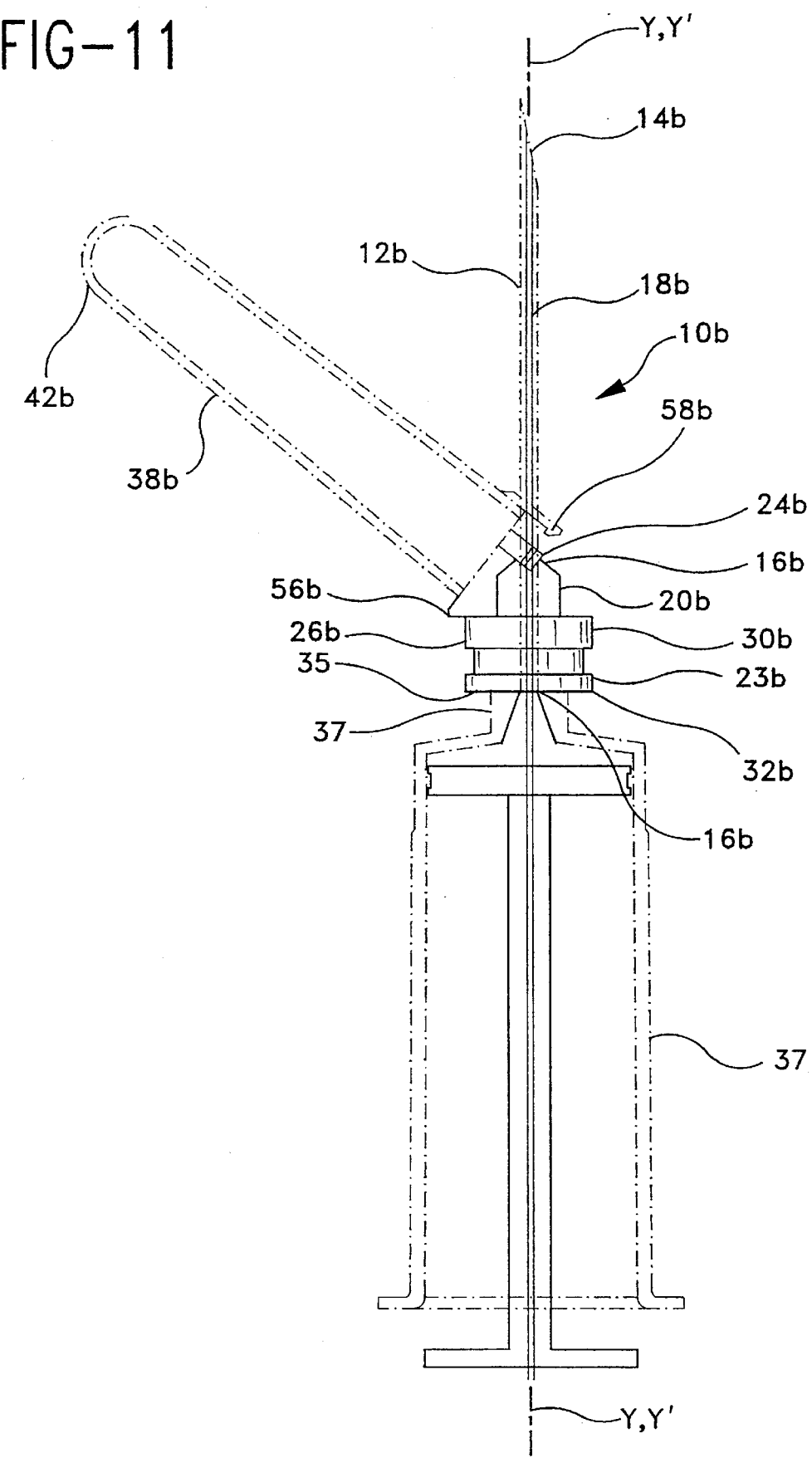
FIG. 11 is an exploded perspective view of an embodiment of the present invention mounted on a syringe with the shield between the first position and the second position.

Preferably, hub 20 also includes elements 32 for releasably mounting the hub onto a fluid handling, i.e., medical delivery, device. In one embodiment where the fluid handling device is a needle tube holder 34, elements 32 are preferably male threads 36 on proximal end 22 for mounting the hub on tube holder 34. Alternatively, as seen in FIG. 11, the elements 32 may be configured to attach the hub 20 onto a syringe or similar medical delivery device. Here, needle assembly 10b includes a needle 12b having a longitudinal axis Y, a pointed distal end 14b, a proximal end 16b and a passageway 18b therethrough. In this embodiment, elements 32b preferably include a female luer lock fitting 35 for mounting the hub on a syringe 37 or other fluid handling device such as a catheter.

Figure 6:
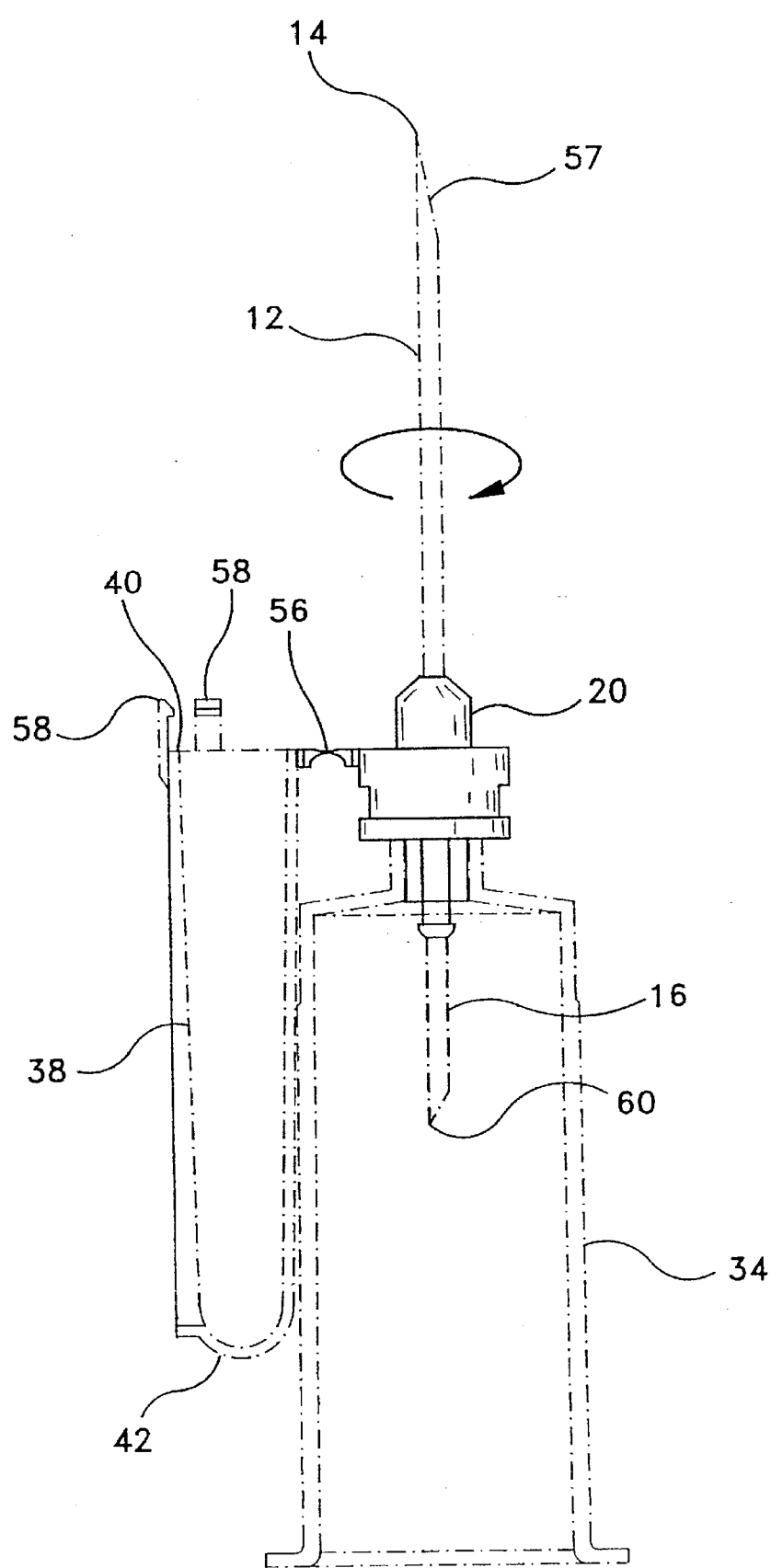
FIG. 6 is a schematic cross sectional view of the embodiment of FIG. 1 mounted on a needle holder with the shield in the first position.
Figure 7:
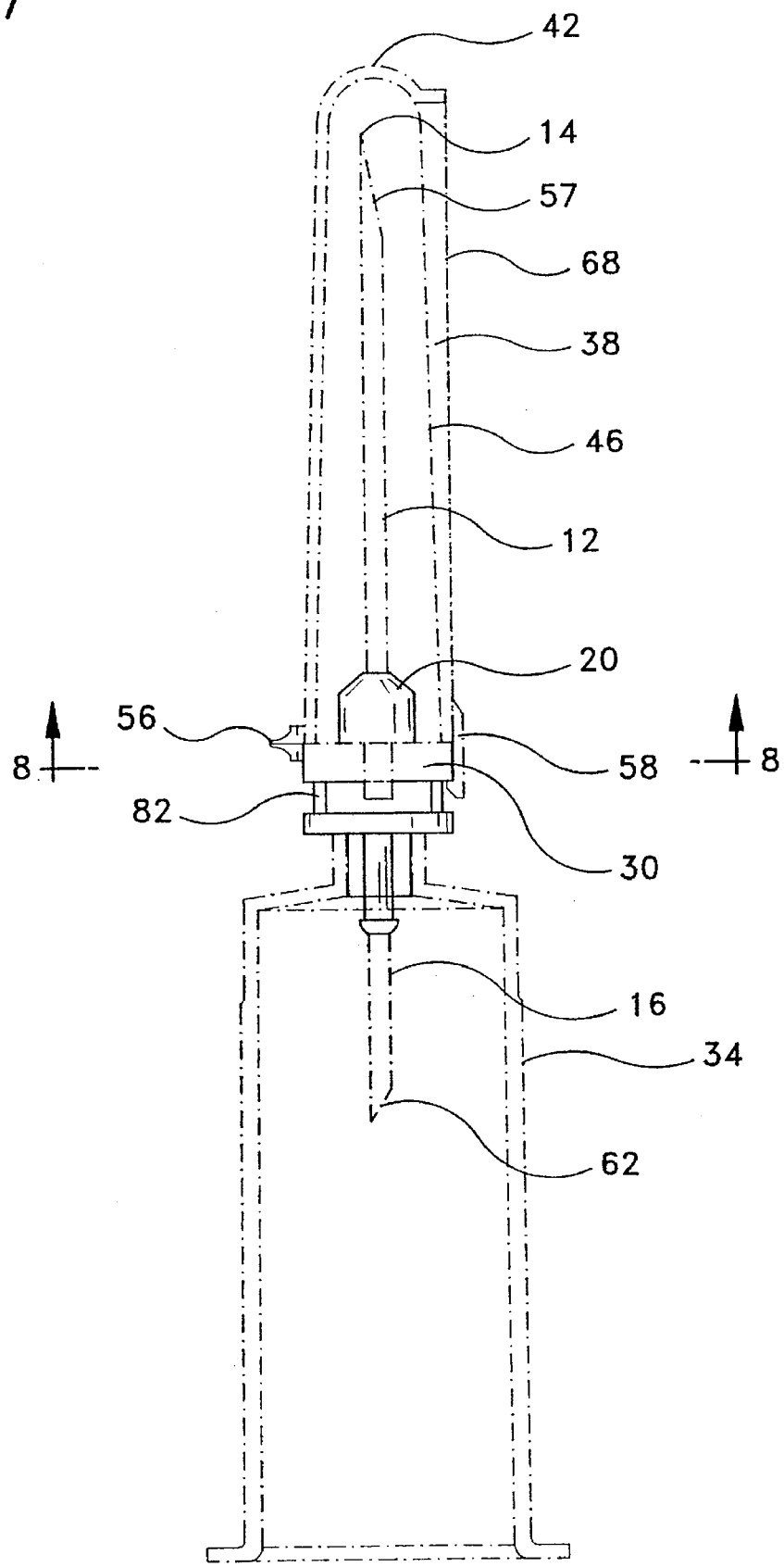
FIG. 7 is a schematic cross sectional view of the embodiment of FIG. 6 with the shield in the second position.

Needle assembly 10 preferably further includes a shield 38 having an open end 40, a closed end 42, and a sidewall portion 44 defining an open slot 46 extending a length "d" from open end 40 toward closed end 42. As illustrated in FIG. 6, shield 38 has a first position at which needle 12 is exposed for use. FIG. 7 illustrates shield 38 in a second position at which shield 38 substantially obstructs unintentional access to needle 12. Shield 38 further preferably includes a mounting 48 for holding shield 38 onto hub 20. The mounting may feature a first portion 50 having an opening 52 therethrough for placement onto the hub at groove 28.

It will be evident to the skilled artisan that hub 20 and mounting 48 can be separately formed and thereafter attached together such as by mechanical means, adhesives, welding, or the like. Alternatively, they may also be made or molded integral with one another. It will also be evident that hub 20 and mounting 48 can be attached (or formed) in a fixed manner relative to one another. However, in order to provide ready orientation of the bevel associated with the tips of most piercing elements, the shielded needle assembly can incorporate according to the invention a rotating mechanism between the hub and the mounting. One way to incorporate rotation includes, for instance, providing hub 20 with a circumferential groove 28 in outside surface 26 with an outside diameter "b" which is less than hub outside surface diameter "a." Hub 20 may also include a raised annulus 30 with an outside diameter "c" which is greater than hub outside surface diameter "a." As part of a way to incorporate a rotating mechanism, opening 52 preferably includes at least one inward projection 54 sized to fit within groove 28 for holding mounting 48 on hub 20 while allowing free rotation of the mounting about the hub. First portion 50 may also feature a hinge 56 attached to shield 38 at open end 40 diametrically opposite slot 46.

A particular benefit of the rotatable mounting for shield 38 is that the shield may be rotated about hub 20 so that the shield does not interfere with a procedure such as blood drawing. The technique practiced by phlebotomists in venipuncture generally requires that the distal point of the needle be aligned so that a face 57 of the beveled needle point 14 is up (away from the patient). This bevel placement allows the needle point to be precisely positioned for the puncture. In performing the penetration of the vein, the goal is to minimize the angle of entry. A minimum angle of entry reduces the incidence of penetration of the far wall of the vein in the venipuncture. Most other shield devices are attached to the tube holder or to the hub with a fixed pivot and the like, thus requiring careful orientation of the needle point to the hub during the manufacture of the device. The need for point orientation imposes an additional and critical requirement on the device manufacturing process, adding an additional step, potentially slowing the rate of manufacture and possibly decreasing the yield. Since the shield rotates about the hub, the present invention requires no orientation of the needle point during manufacture, retaining the process and equipment currently used for conventional needle assemblies.

The clearance provided by slot 46 allows shield 38 to pivot on hinge 56 from the first position to the second position, where the shield can engulf the needle so as to avert inadvertent touch contact with same and, in particular, can obstruct access to the distal tip of the needle. Shield open end 40 may also further include at least one lug 58 for engaging annulus 30 when shield 38 is in the second position.

In a preferred embodiment where assembly 10 is intended for use in a needle holder, proximal end 16 of the needle preferably projects outwardly from hub 20 and includes a proximal point 60 for penetrating a stopper of a fluid collection tube. One skilled in the art of medical devices will recognize that needle 12 may be formed as a single article having a proximal point on a proximal portion projecting proximally and a distal point on a distal portion projecting distally. Alternately, needle 12 may be formed in two separate pieces, a distal piece projecting distally having a distal point and a proximal piece projecting proximally having a proximal point, with the pieces connected in fluid communication in the hub opening. Preferably, safety needle assembly 10 includes a removable distal cover 62 releasably mounted on hub 20 for covering needle 12 projecting distally from the hub. Distal cover 62 provides physical protection for distal point 14 and may serve as a barrier to passage of microorganisms until it is removed prior to use. Assembly 10 preferably includes a removable proximal cover 64 mounted on hub 20 for covering proximal needle end 16 projecting from the hub. Proximal cover 64 provides physical protection for proximal point 60 and may provide a barrier to passage of microorganisms until the proximal cover is removed.

Assembly 10 preferably is sealed in a package (schematically illustrated as reference number 80 in the drawings) formed from materials resistant to the passage of microorganisms and exposed to conditions that render any microorganisms present in the package substantially nonviable. Generally, in the medical device industry, exposure of a packaged device to ethylene oxide or to beta or gamma radiation is used to render microorganisms nonviable and the device within the package is defined as sterile. A packaged safety needle assembly would be sterile until package 80 was opened for use. Additionally, covers 62 and 64 serve to keep needle 12 sterile until they are removed for immediate use.

Slot 46 in the sidewall of shield 38 has a perimeter 66 which preferably includes a raised rib 68. Raised rib 68 serves to stiffen shield 38 and to substantially reduce incidence of spatter from any residual fluid on needle 12 when the shield is in the second position.

As will be realized by the skilled artisan, shield 38 and mounting 48 with first portion 50 and hinge 56 may be formed as a unitary article of manufacture. Hinge 56 may be formed as a "living hinge" when the shield and mounting are formed as a single unit. Preferably shield 38 and mounting 48 are formed by injection molding a thermoplastic resin. It is well known in an injection molded article that, if an area of the article has a reduced thickness relative to its surrounding area and the molded part is flexed at the area of reduced thickness immediately after the part is removed from the injection molding tool, the area of reduced thickness functions as a hinge because the polymer molecules of the resin are oriented by the flexion. If the article is not flexed immediately, the ability to form a hinge is lost, hence the term "living hinge." In a preferred shield and mounting in accordance with one embodiment of the present invention, hinge 56 includes a strip 70 with an area of reduced thickness 72 which is preferably formed into a living hinge when the article is freshly removed from the mold tool.

FIG. 3 shows an alternate embodiment to the hinge similar to the cross-sectional view illustrated in FIG. 2. In this embodiment, there are elements similar in structure and function to the embodiment of the present invention shown in FIG. 1. Accordingly, substantially similar components that perform substantially similar functions are numbered identically to those components of the embodiment of FIG. 1 except that a suffix is added to identify those components in FIG. 3. As shown in FIG. 3, shield 38a and mounting 48a may be individually formed and joined by hinge 56a which includes rotatable mechanical elements such as pins 74 mounted in recesses 76. The actual form of the mechanical hinge is not critical to the invention. Other types of rotatable mechanical hinges are also satisfactory.

Shield 38 and mounting 48 may be formed from thermoplastic resins such as polyvinyl chloride, polystyrene, polypropylene, polycarbonate, polyethylene and the like. Polypropylene, polyethylene, and copolymers of polypropylene and polyethylene are preferred, as they are particularly suited for the formation of living hinges.

Shield 38 preferably has at least one lug 58 and, as illustrated in FIG. 1, here two lugs 58 to engage annulus 30 when the shield is in the second position. When lugs 58 engage annulus 30, shield 38 is locked in the second position, substantially preventing inadvertent contact with needle 12.

In normal usage of this embodiment of the needle assembly for drawing a blood sample, proximal cover 64 is removed from the assembly and hub 20 mounted in needle holder 34 using threads 36. Immediately prior to the procedure, distal cover 62 is then removed exposing needle point 14. Face 57 of the beveled needle is aligned to face away from the patient. During the alignment, the practitioner rotates shield 38 around hub 20 so as not to interfere with the placement of the needle point. The precise position allows the practitioner to minimize the angle of entry of the needle into the vein. A minimum penetration angle reduces the incidence of penetration of the needle through the far wall of the vein. Needle point 14 is then inserted into the patient's vein and an evacuated blood collection tube with an elastomeric stopper is mounted in the needle holder so that its stopper is penetrated by proximal needle point 60. When the practitioner has completed the blood drawing, the needle is withdrawn from the patient's vein and shield 38 is moved to the second position, obstructing needle 12. As shield 38 is moved to the second position, slot 46 provides clearance for the shield to pass over the needle. Lugs 58 engage annulus 30 when the shield is in the second position and lock shield 38 in the second position.

Figure 8:
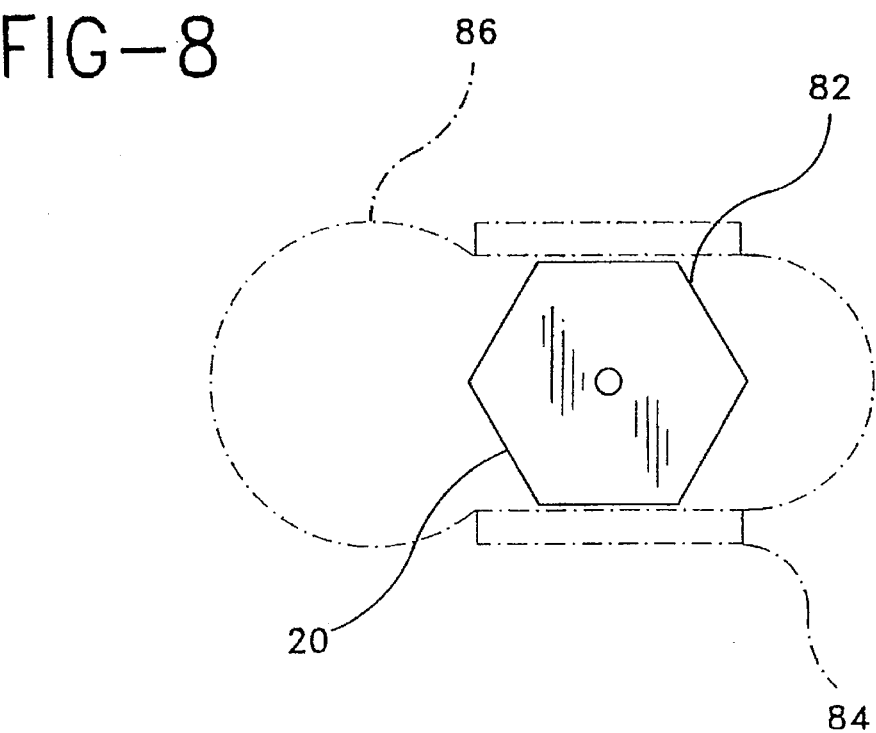
FIG. 8 is a partial schematic cross sectional view along the line 8,8 of the embodiment of FIG. 7 mounted in a needle removal device.
Figure 9:
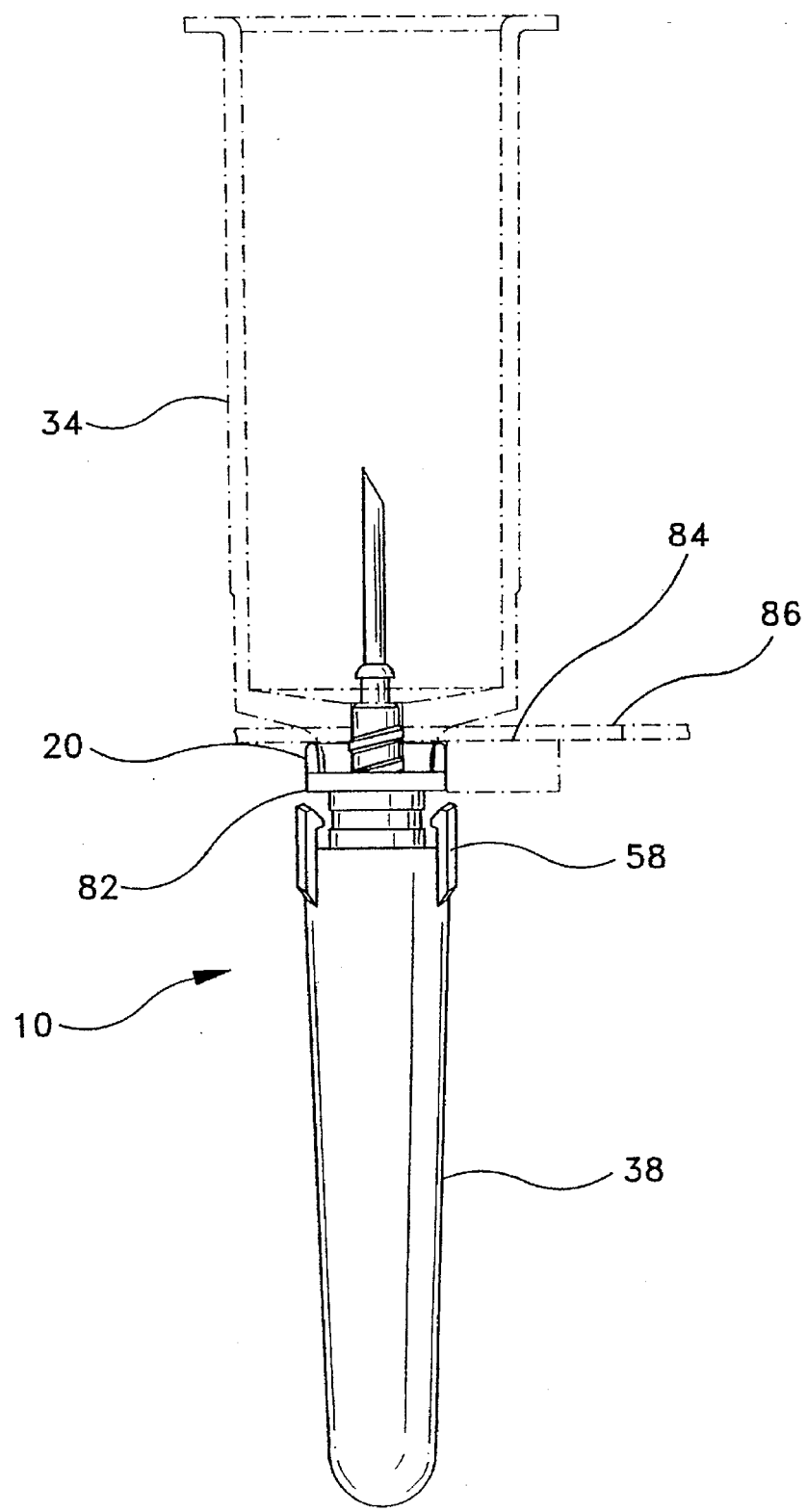
FIG. 9 is a schematic cross sectional view of the embodiment of FIG. 7 mounted in the needle removal device.
Figure 10:
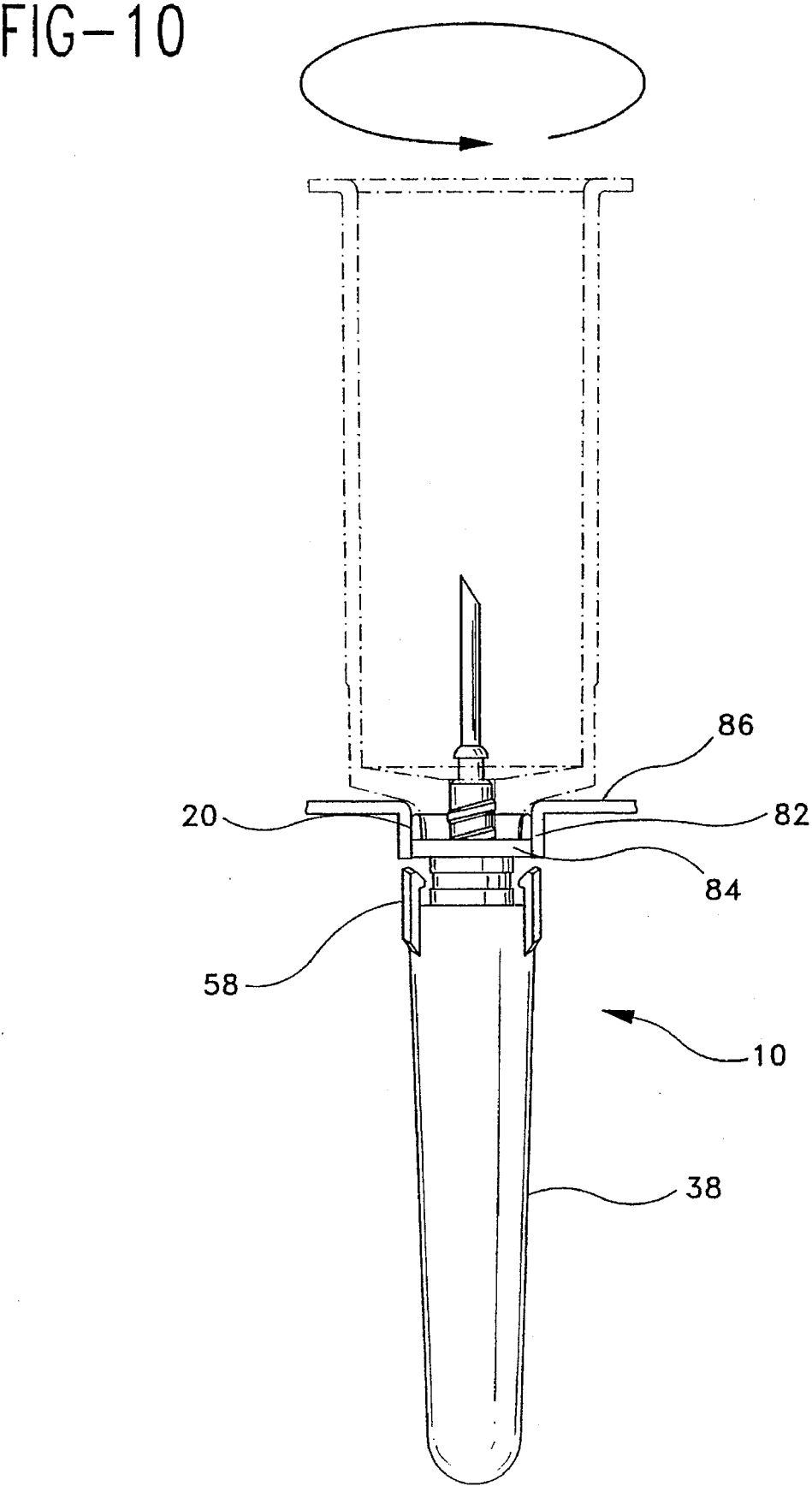
FIG. 10 is a cross sectional view of the embodiment of FIG. 9 mounted in the needle removal device.

Referring to FIGS. 8, 9 and 10, hub 20 preferably has a proximal faceted area 82. As here illustrated, faceted area 82 is hexagonal in shape. Faceted area 82 is designed to engage a wrench opening 84 of a safety needle container 86 after the blood drawing procedure is completed and shield 38 is in the second position. The practitioner holds the needle holder and places the needle assembly with shield in the second position into the safety needle container so that faceted area 82 engages the wrench opening of the safety needle container. Needle holder 34 can be easily unscrewed and the needle assembly allowed to fall into the collector for safe disposal. Use of needle assembly 10 imposes little additional requirement on the practitioner. Except for moving shield 38 from the first position to the second position, all the other steps of the blood draw procedure follow normal accepted practice, and needle holder 34 is the standard currently available commercial product.

FIGS. 11-26 generally detail the protective barrier assembly of the present invention applied, for instance, to a fluid delivery device such as a syringe or catheter. In general, FIG. 11 depicts the embodiment explained hereinabove with reference to FIGS. 1-10, and thus there are elements similar in structure and function as those explained with reference to those figures and particularly FIGS. 1-7. Accordingly, substantially similar components that perform substantially similar functions are numbered identically to those components of the embodiment of FIGS. 1-7 except that a suffix will be added to identify those components.

Thus, as shown in FIG. 11, needle assembly 10b includes a needle 12b having a longitudinal axis Y, a pointed distal end 14b, a proximal end 16b and a passageway 18b therethrough. In this embodiment, elements 32b preferably include a female luer lock fitting 35 for mounting the hub on a syringe 37 or other fluid handling device such as a catheter.

Turning now to FIGS. 12-26, alternate embodiments of the protective barrier assembly of the present invention are depicted, inclusive of various embodiments of locking assemblies which provide for secure locking of the shield 38 with respect to the needle 12. In addition, alternate embodiments of locking and closure assemblies for the protective barrier assembly of the present invention are disclosed. These assemblies provide both a secure closure position, enabling the shield to be releasably held over the needle 12 during interim use of the device, as well as a secure locking position of the shield 38 relative to the needle 12 so as to prevent a used needle 12 from being exposed against inadvertent touch contact by the user.

Figure 12:
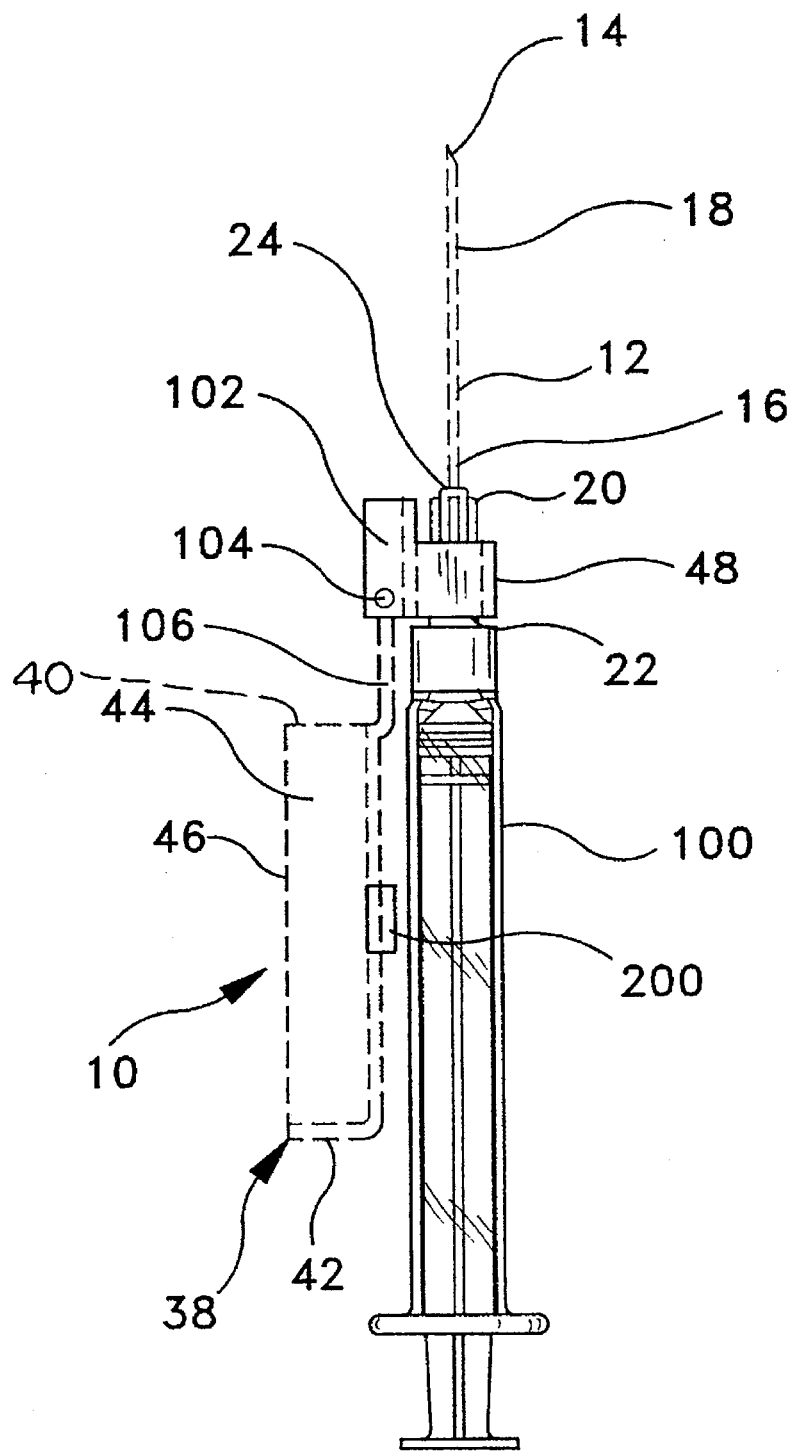
FIGS. 12 and 13 depict in perspective view an alternate embodiment of the safety needle assembly of the present invention in conjunction with a syringe.
Figure 13:
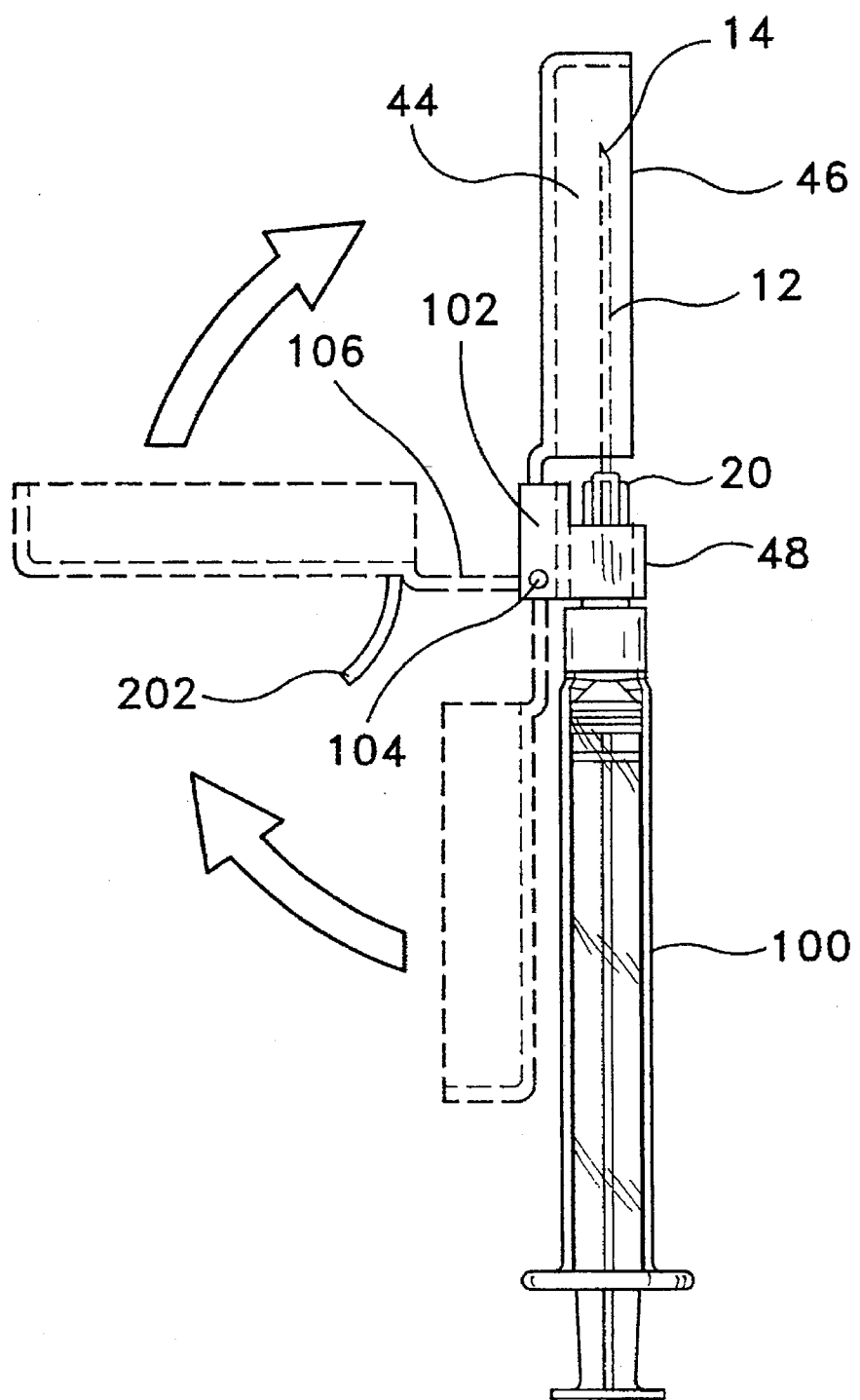

FIGS. 12 and 13 generally depict the safety needle assembly of the present invention in conjunction with a medical delivery device such as a syringe 100. It will be understood and appreciated by those skilled in the art that while these embodiments of the safety needle assembly of the present invention are depicted in conjunction with a syringe, they may be equally applied to other medical delivery devices such as a catheter, or to a fluid collection device such as a needle tube holder 34 previously described.

Here, shield 38 also includes a generally open end 40, a closed end 42, and a side wall portion 44 extending, for instance, on three sides of the shield 38. A longitudinal slot 46 is defined within the side wall portion 44 and is formed, for instance, to accommodate needle 12 within the interior of the shield 38. As seen in FIG. 12, a flange 200 may be incorporated into the structure of the shield 38 to assist the user in operating the device. A tab element 202 (FIG. 13) may be provided, for instance, near arm 106 for the same purpose.

Figure 39:
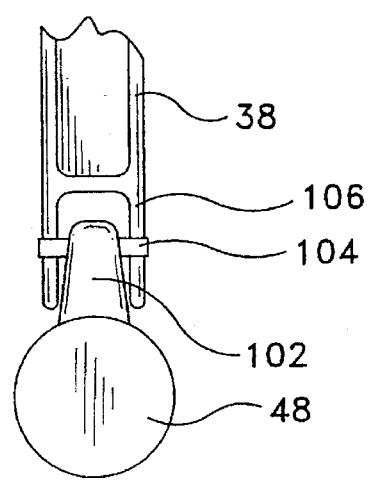
FIG. 39 depicts an alternate way to pivot the shield to the collar mounting.

As herein shown, shield 38 is hingedly affixed by an arm portion 106 via a pivot 104 mounted to a hinge portion 102 of mounting collar 48. While herein depicted as a pivot pin 104, it will be appreciated and understood by those skilled in the art that, if desired, arm 106 can be formed directly with hinge portion 102 and a living hinge formed in lieu of the pivot 104, all as previously described hereinabove. It will also be appreciated and understood by those skilled in the art that hinge portion 102 and collar mounting 48 may be unitarily formed, and the sheath 38 formed unitarily with them or as a separate component. Likewise, the collar portion 48 may be formed unitarily with hub 20 or they may be formed as separate parts and then attached to one another, for instance, via adhesives, welding, bonding or mechanical affixation methods within the realm of the skilled artisan. Moreover, if desired, collar mounting portion 48 and hub 20 may be configured for rotatable interaction, for instance, in a manner as previously described hereinabove. As depicted in FIG. 39, if desired arm portion 106 can be configured to surround hinge portion 102, the pivot pin 104 laterally passing through hinge portion 102 and through opposing, surrounding sides of arm portion 106.

Figure 14:
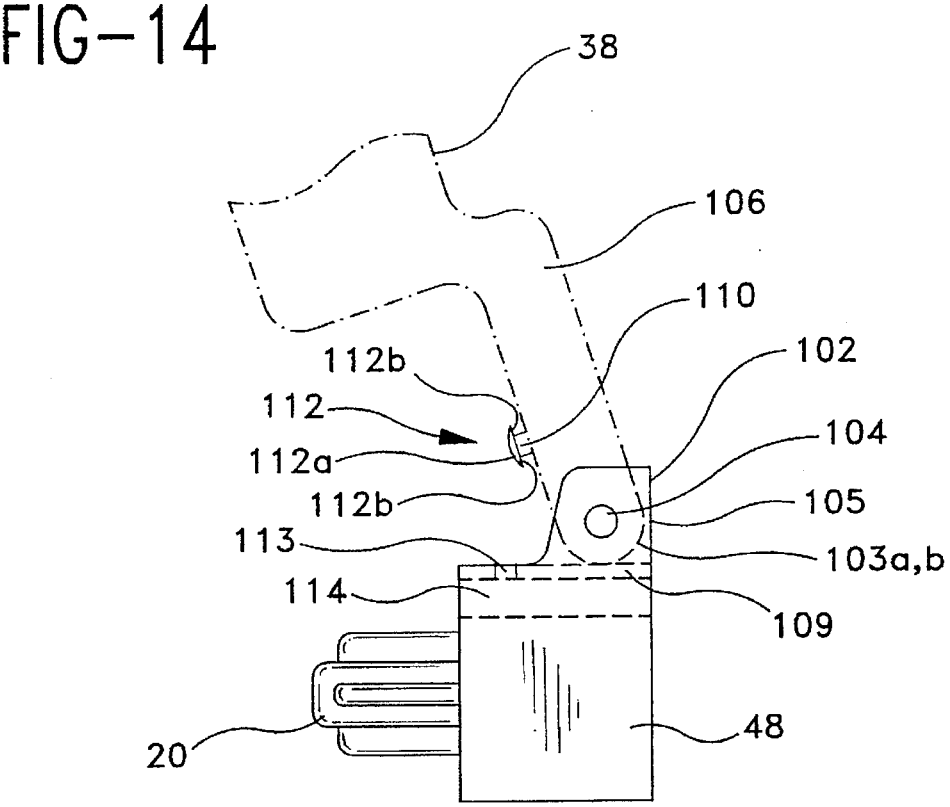
FIGS. 14 and 15 depict one embodiment of a locking assembly for a safety needle assembly in accordance with the subject invention.
Figure 15:
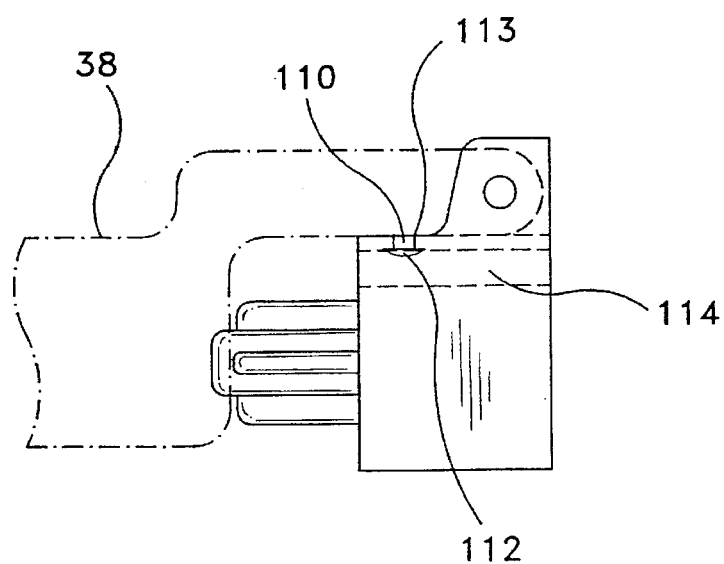

Turning now more particularly to FIGS. 14-28, numerous embodiments of locking mechanisms (FIGS. 14-20) or closing and locking mechanisms (FIGS. 21-28) are herein described. Referring to FIGS. 14 and 15, one embodiment of a locking mechanism for use with a safety needle assembly of the present invention is disclosed. Here, hinge portion 102 is affixed to the side of collar mounting 48 and is formed, for instance, as a pair of parallel side walls 103a, b which define a channel 105 thereinbetween. Arm portion 106 is pivotably mounted between sidewalls 103a, b within the channel 105 via pivot pin 104. A second channel 114 may be defined between collar mounting 48 and hinge portion 102, for instance, via a wall portion 109 dividing the hinge portion 102 from the overall collar mounting 48.

As illustrated, a hole or opening 113 may be formed through the wall portion 109, distally of the pivot point defined by pivot 104. A locking pin 110 is provided on the arm portion 106 of shield 38, with the pin including a mushroom-shaped head 112 at the tip of pin 110. As shown, mushroom shaped head 112 is wider than the shaft of pin 110. While here shown that locking pin 110 is formed on the arm 106 while opening 113 is formed through wall portion 109, it will be evident to the skilled artisan that pin 110 can be provided in conjunction with channel 105 or hinge portion 102 while hole 113 can be formed on arm 106. Also, while here shown that head 112 is mushroom-shaped, it will be evident to the skilled artisan that other shapes such as barbs, arrowheads, and the like can also be employed.

As illustrated, the mushroom-shaped head 112 of the pin 110 is configured slightly wider than the hole 113 disposed through wall 109. Thus, when the shield is pivoted to the locked position illustrated in FIG. 15, the mushroom-shaped head will be compressed through the hole 113 and re-expand as it enters channel 114. The head will thus be thrust flush against the wall 109 so as to prevent the shield 38 from being re-pivoted to re-expose the needle piercing element 12. Note that the rounded head surface 112a of mushroom-shaped head 112 facilitates compression of the head through hole 113 as the shield is rotated into a locked position, but the flat back surfaces 112b of the pin will be engaged against the wall portion 109 surrounding hole 113 subsequent to locking and contribute to the pin's retention with the collar mounting 48. Note also that pin 110 itself or at least its mushroom-shaped head 112 should be formed from a material which is somewhat resilient so as to be compressed through hole 113 as the lever arm 106 is rotated into locked position, but which will resist recompression through hole 113 to prevent shield 38 from being reversed to the open position. For instance, polypropylene may be employed.

Figure 16:
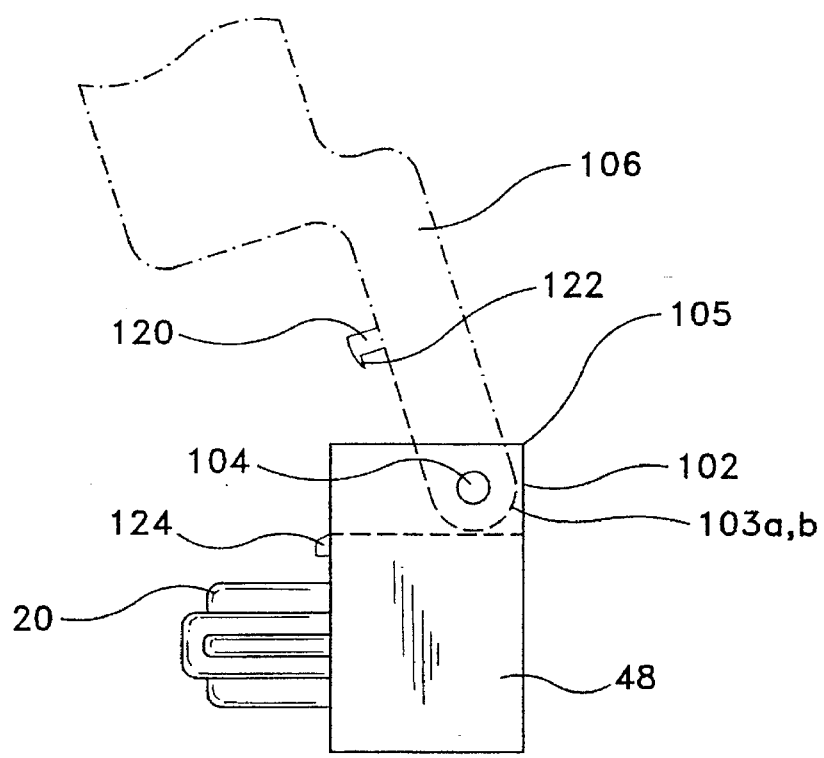
FIGS. 16 and 17 depict an alternate embodiment of a locking assembly for a safety needle assembly in accordance with the subject invention;.
Figure 17:
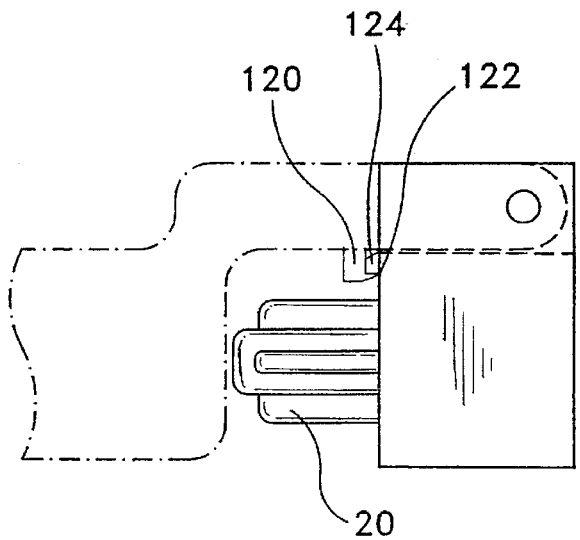

FIGS. 16 and 17 depict another embodiment of a locking mechanism for use with a safety needle assembly of the present invention. Again, arm 106 is pivotably connected to hinge portion 102 in a channel 105 formed by parallel plates 103a, b. A locking pin 120 is disposed, formed, or otherwise affixed to arm portion 106 at a point distal from pivot 104. The locking pin 120 features a hooked end 122 configured to be retained by a protrusion or detent element 124 formed on the collar mounting 48. Thus, as seen in FIG. 17, when shield 38 is rotated into the locked position, hooked end 122 is urged over the detent element 124 to be retained beneath and against the protrusion 124, thereby irreversibly locking the shield 38 in a secure position relative to needle 12.

Figure 18:
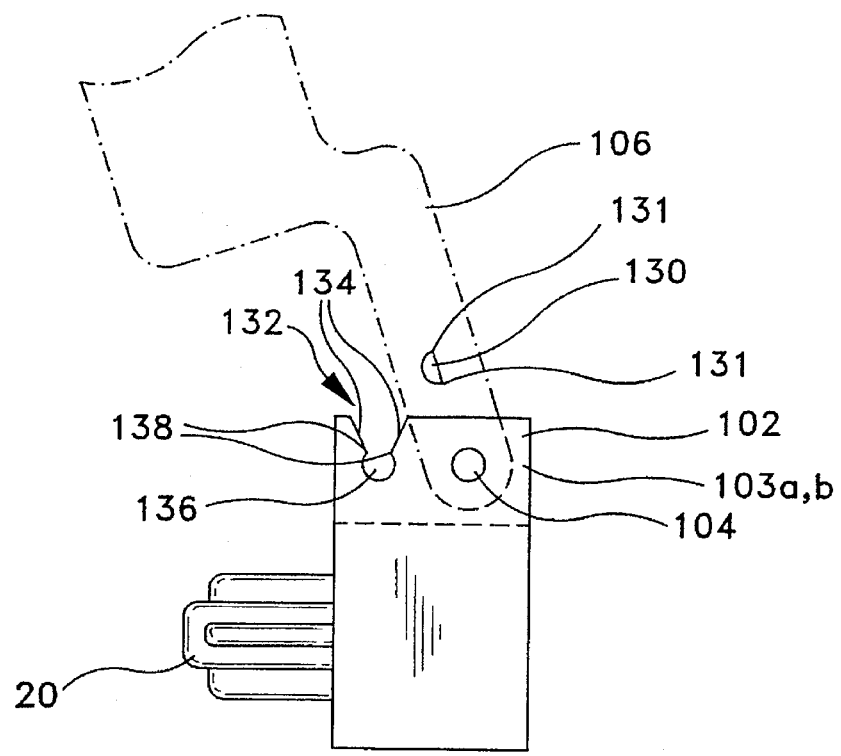
FIGS. 18–20 depict an additional embodiment of a locking assembly for a safety needle assembly in accordance with the subject invention.
Figure 19:
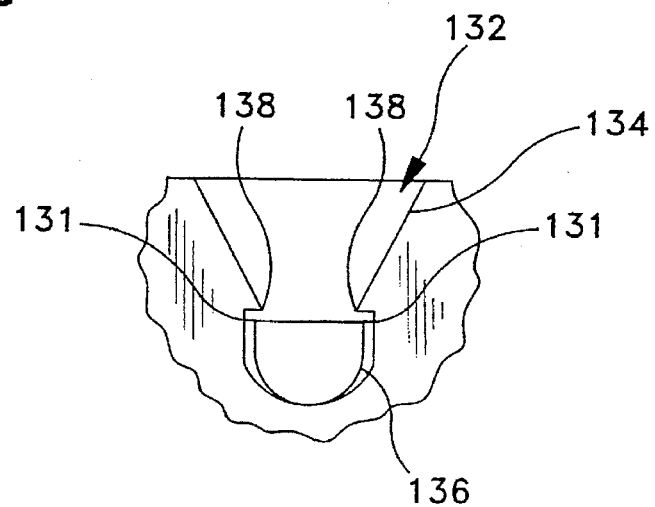
Figure 20:
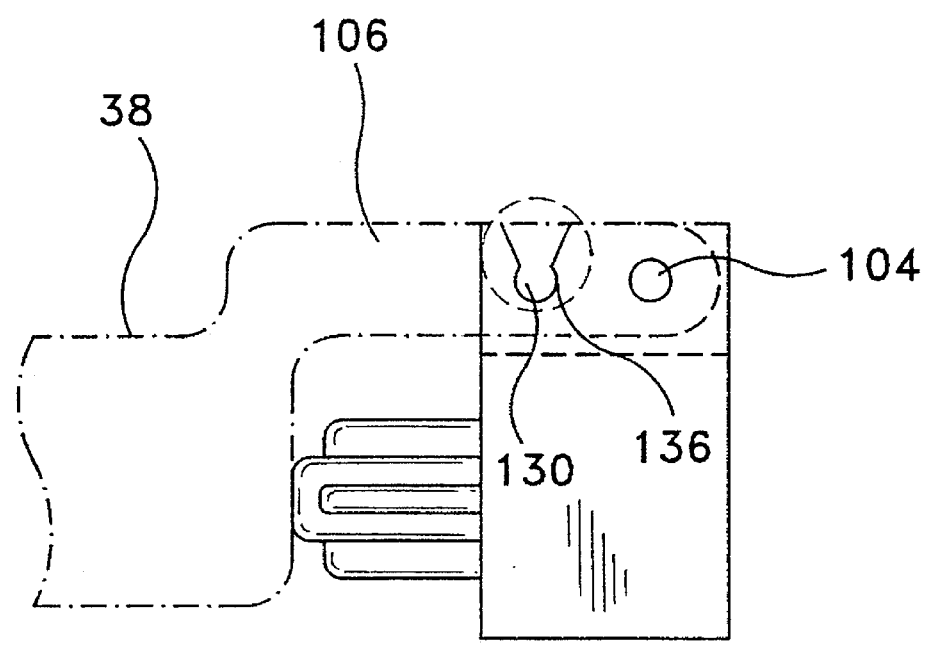

Another form of a locking mechanism for use with the present invention is depicted in FIGS. 18–20. As before, arm 106 is pivotably affixed to hinge portion 102 which is formed, for example, as a pair of side plates 103a, b defining a channel 105 therewithin. In this embodiment, a protruding locking pin 130 can be formed, disposed, affixed, or otherwise placed on either of or both sides of the arm 106 at a location distal from hinge point 104. Pin 130 can be formed of a compressible material such as, for instance, polypropylene, polycarbonate, polystyrene, or materials with like properties. The pin (or pins) 130 are disposed to be retained within a hole or opening 132 cut, formed, or molded within either of or on both of side plates 103a, b. It will also be understood by the skilled artisan that opening 132 need not extend through the width of plates 103a, b, but that they may be formed as gouges in plates 103a, b, such as by routing through only a portion of the width of the plates 103a, b and not entirely through the width of the plates.

As illustrated, opening 132 features a pair of sloping lead walls 134 formed in a roughly "V" configuration to guide pin 130 into a receptacle portion 136 located at the bottom of the opening 132. As also illustrated, receptacle portion 136 may be formed somewhat semi-circular in shape so that transition edges 138 located at the intersection between sloping walls 134 and the receptacle 136 define a width between them which is narrower than the diameter of the receptacle.

When in the locked position of FIG. 20, the pin (or pins) 130 will be disposed in receptacle 136, as best illustrated in FIG. 19. Note that when the shield is rotated into locked position, pin 130 will be guided by the sloping walls 134 to compress past the edges 138 so as to be lockingly disposed within receptacle 136. Also note that in the form depicted, the pin 130 has a pair of edges 131 which define a width greater than the width between transitional edges 138 of the hole 132, but which are somewhat narrower than the diameter of receptacle 136 so as to permit the pin to be retained there. Thus, edges 131 of pin 130 will be thrust beneath edges 138 of hole 132 to permanently lock shield 38 into the locked position once so rotated.

It will, of course, be understood by the skilled artisan that if desired, in lieu of a pin with compressible properties, pin 130 can be formed of a relatively rigid material and plates 103a, b of a more compressible material so that edges 138 are free to expand to accept the pin 130 in the receptacle 136 and thereafter re-compress so as to retain the pin in the receptacle. Furthermore, as with the embodiment depicted at FIGS. 14 and 15, pin 130 can be provided in conjunction with plates 103a, b while the receptacle 136 can be formed with arm 106.

FIGS. 21–28 depict various embodiments of so-called "closing and locking" mechanisms for use with the subject invention, with a distinct component providing a secure but releasable closing position, and a separate component providing a more permanent locking position. It will be expressly understood by the skilled artisan that, if desired, the "locking" component of each of these embodiments may be omitted so as to provide embodiments having secure but releasable closing positions particularly useful, for instance, when frequent use of a piercing element is experienced pending final use of the product. Thus, in each of the following embodiments, it is expressly understood that they are intended to also encompass embodiments capable of repeated opening and closing from the secure, but releasable, closing position.

Figure 21:
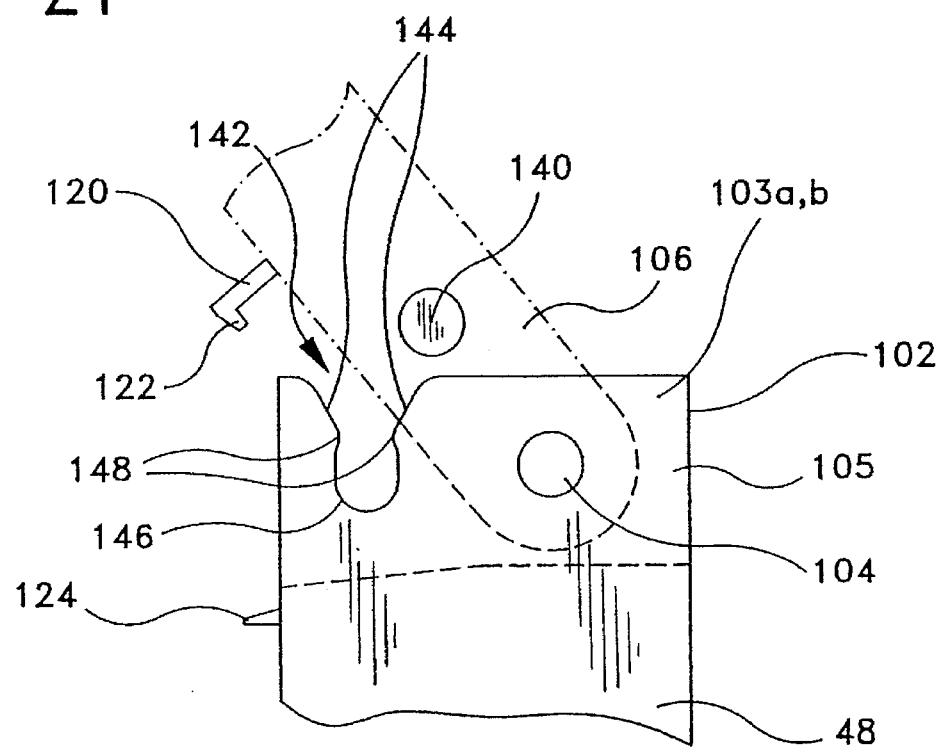
FIGS. 21–23 depict one embodiment of a closure and locking assembly for a safety needle assembly in accordance with the present invention useful for providing a secure interim closing position and a locking position.
Figure 22:
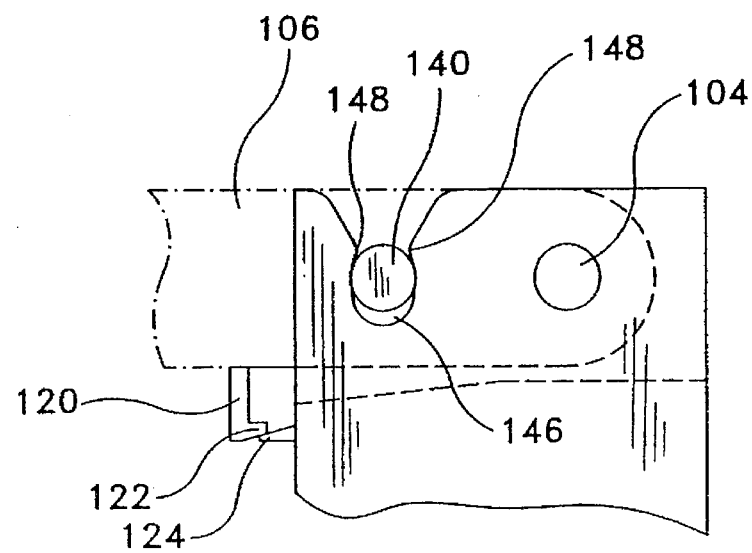
Figure 23:
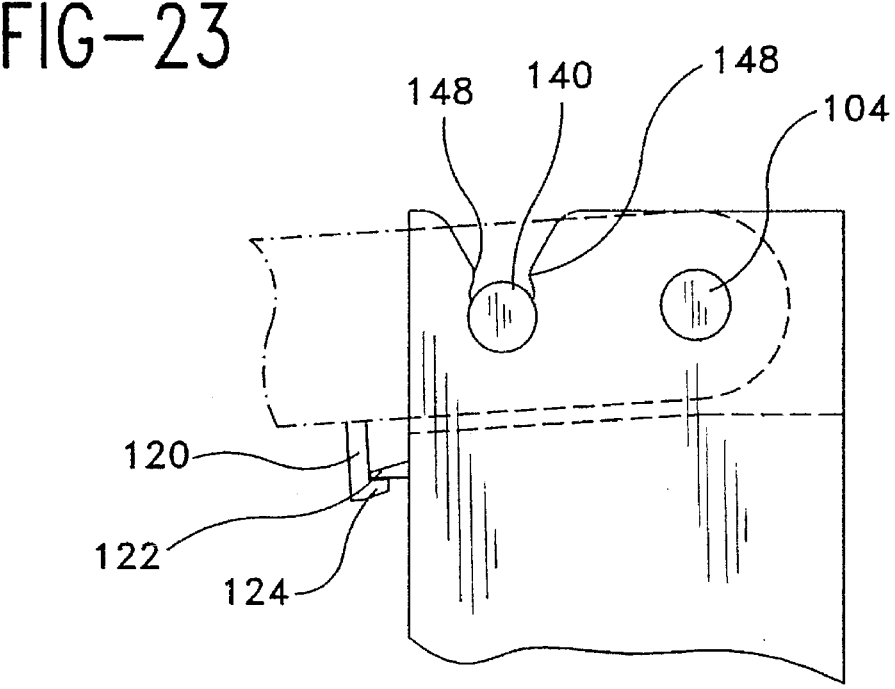

Accordingly, there is depicted in FIGS. 21–23 one embodiment of a closing and locking mechanism for the safety needle assembly of the present invention. In this embodiment, the shield 38 is provided with at least two distinct positions in which to secure needle 12 from inadvertent touch contact. The first is a "closed" position, which is typically an interim position of the shield pending final use which will shield the needle but which will allow a user to expose the needle for further use. The second position is a fully "locked" position, wherein the sheath will be permanently locked into position to prevent re-exposure of the needle. As depicted in FIG. 22, arm 106 is pivotably attached to hinge portion 102 between a pair of parallel side plates 103a, b as previously described. A protruding pin 140 may be provided on either of or on both sides of the arm 106 at a location distal from hinge 104, with the pin (or pins) formed to be retained within a hole (or holes) 142 formed in either or both of the side plates 103a, b. As with the embodiments of FIGS. 14–15 and 18–20, the positions of pin(s) 140 and hole(s) 142 can be reversed, with pin(s) 140 provided in conjunction with the plates 103a, b and hole(s) 142 provided in conjunction with arm 106.

Hole 142 features a pair of sloping guide walls 144 and terminates in a receptacle portion 146. A pair of protruding edges 148 located at the intersection between sloping walls 144 and receptacle 146 define a width between them which is less than the diameter of the receptacle 146. In addition, arm 106 features a locking hook 120 having a curved hook end 122 configured to engage a protrusion or detent portion 124 formed on or with mounting collar 48.

As seen in FIG. 22, if a user desires to place the shield 38 in a "closed" position, rotation of the shield 38 can be effected until such point as hooked end 122 engages a top surface of protrusion 124 but is not displaced to such a degree that the hook 122 is urged over the protrusion so as to be retained in a latched position beneath it. Note that as configured, pin 140 has been urged along sloping walls 144 of the hole 142 so as to be frictionally engaged by transitions 148 of the receptacle 146, without the pin 140 being fully enclosed within the receptacle 146. This friction fit between the pin 140 and the receptacle 146, coupled with non-latching of the hook 120 with the protrusion 124, enables the sheath to be securely held in place in a closed position, but a user can still re-expose the needle by pivotable rotation of the sheath 38 which overcomes the frictional force exerted between the pin 140 and protrusions 148, thereby urging pin 140 out of hole 142. However, for the locking position illustrated in FIG. 23, further rotation of sheath 38 will cause hook end 122 to be disposed beneath the protrusion 124 so as to lock the shield in place. Note also that in this position, pin 140 will be fully disposed within receptacle 146, with the narrower width defined between protrusions 148 deterring recompression of pin 140 out of hole 142 and serving as a backup to the locking action of locking hook 120. Of course, as previously explained, deletion of hook 120 or protrusion 124, or both, will serve to produce an embodiment capable of repeated secure but releasable closure of the sheath.

Figure 24:
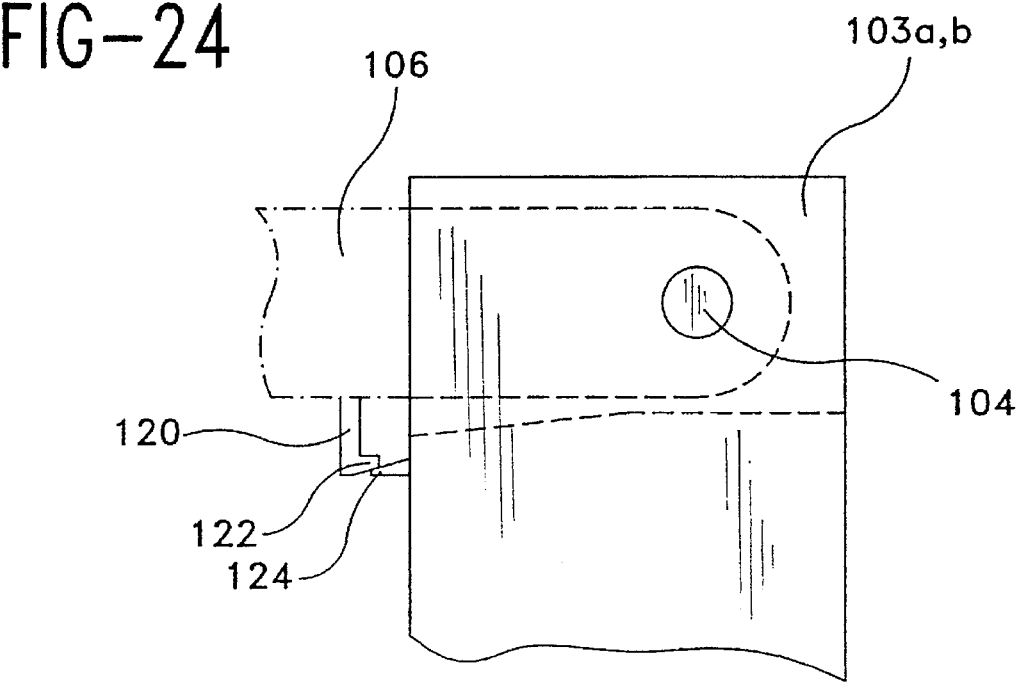
FIGS. 24–26 depict an alternate embodiment of a closure and locking assembly for a safety needle assembly in accordance with the present invention.
Figure 25:
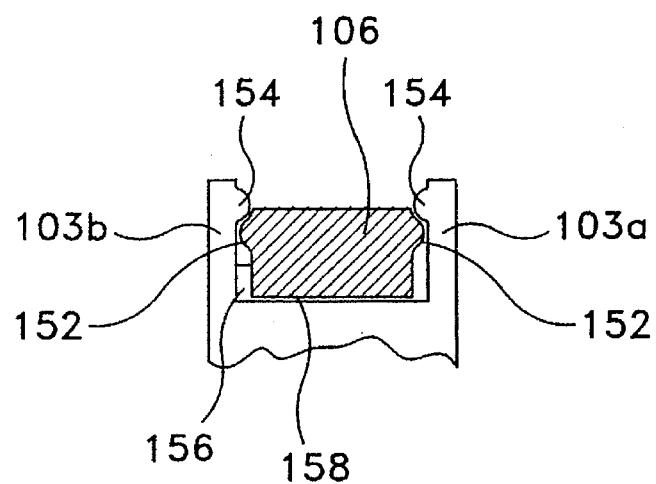
Figure 26:
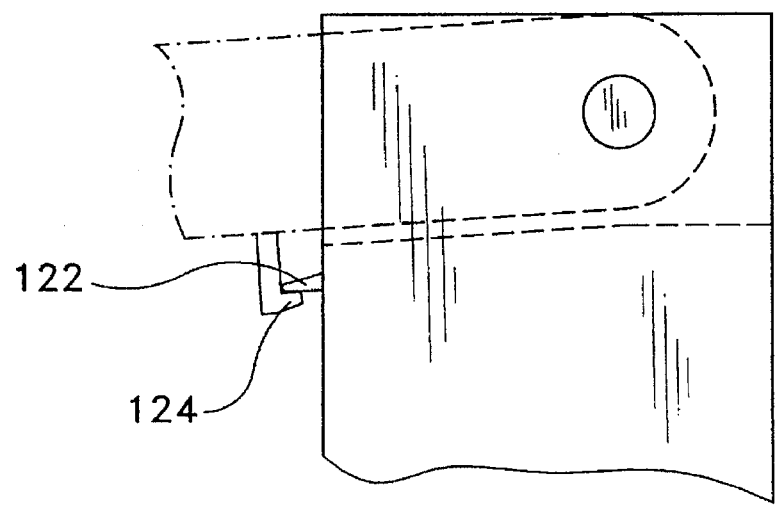

FIGS. 24–26 illustrate a second embodiment of a closing/locking embodiment for the safety needle assembly of the present invention. This embodiment also includes a hook 120 in conjunction with protrusion 124 as previously explained and whose operation can be gleaned from the discussion hereinabove. In lieu of pins 140, however, dosing operation is effected by configuring arm 106 with a cross-section that defines a pair of protrusions 156 disposed for releasable engagement with a second pair of protrusions 154 formed on either (or both) of the inside surfaces of side walls 103a, b. As illustrated in FIG. 25, the respective arm and side wall protrusions 156, 154 can be configured with complimentary shaped surfaces such as curves; squares, sharp edges, or the like so as to enable a user to conveniently re-expose needle 12 with a minimum of effort upon shield 38, the protrusions 154, 156, however, still providing positive closing action between arm 106 and hinge 102 so as to prevent inadvertent re-exposure of a needle. Here, the complimentary shaped surfaces 154, 156 are depicted as curves. Thus, when shield 38 is urged into the closed position as described with reference to the embodiment of FIGS. 21–23 hereinabove, arm protrusions 156 will be disposed beneath the protrusions 154 of the guide walls 103a, b to releasable retain the shield 38 in the closed position. Note that channel 152 can be formed between sidewalls 103a, b is of a size relative to the cross-sectional area of arm 106 so that a gap 158 will exist in the channel 152 when arm 106 is disposed in the closed position. Thus, the locked position of FIG. 26 can be effected without interference between the arm 106 and the channel 152. As before, omission of hook 120 or protrusion 124, or both, will secure to produce an embodiment capable of repeated secure but releasable closures. As will be realized by the skilled artisan, by removing hook 120 or protrusion 124, or both, the gap 158 need not be incorporated, as need or desire dictate, in order that a tighter, more play-free fit can be effected between arm 106 and channel 152.

Figure 27:
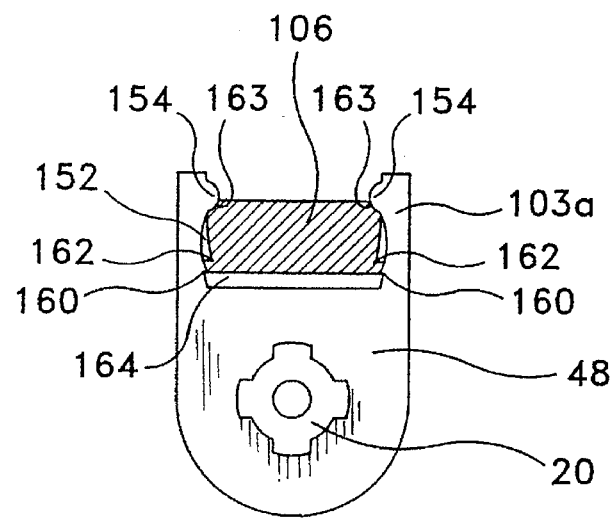
FIGS. 27 and 28 depict an additional embodiment of a closure and locking assembly for a safety needle assembly in accordance with the present invention.
Figure 28:
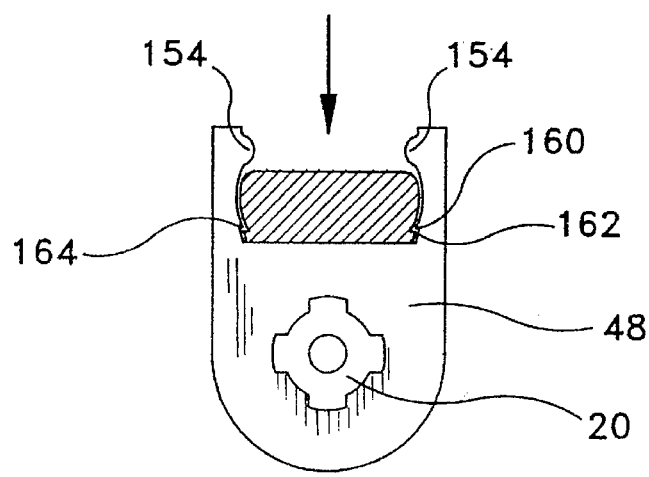

FIGS. 27 and 28 depict yet another embodiment of a closing/locking mechanism for the safety needle assembly of the present invention. This embodiment can be used with or without the hook 120 of the embodiments previously described. Here, side walls 103a, b define a channel 152 having a first set of protrusions 154 at the top end of the side walls 103a, b, with a bottom-most set of protrusions 160 in the channel 152 disposed to form a second channel area 164 slightly wider than the width between the bottom-most protrusions 160. Arm 106 is configured in cross-section to include a pair of top edges 163 engageable against the top-most protrusions 154 of the side walls, and a pair of protruding bottom edges 162 disposed to be retained in a locking manner beneath bottom-most channel protrusions 160. In the closed position illustrated in FIG. 27, the protruding bottom edges 162 of the arm are disposed above bottom-most channel protrusions 160, while top-most edges 163 of arm 106 are disposed beneath protrusions 154 of the side walls 103a, b to provide a releasable closing force as previously described. Further locking rotation of the shield 38 will urge arm 106 further down into the bottom-most channel 164. The protruding bottom-most edges 162 of the arm 106 will then be thrust into the channel 164 to lockingly retain arm 106 therewith by the action of arm edges 162 thrust beneath bottom-most channel protrusions 160. As before, by forming arm 106 without bottom edges 162, by deleting channel 164, by deleting channel protrusions 160, or by effecting any of the three in combination, there would result an embodiment capable of repeated secure but releasable closure.

As explained previously, deletion of the locking component of the embodiments depicted in FIGS. 21–28 will result in embodiments of the invention capable of repeated secure but releasable closure of the shield 38 to protect the piercing element 12 from inadvertent touch contact. There are, however, depicted in FIGS. 29–31, 32–33 and 34–35, respectively, alternative embodiments of the subject invention particularly directed to secure repeated but releasable closure of the shield with respect to the piercing element.

Figure 29:
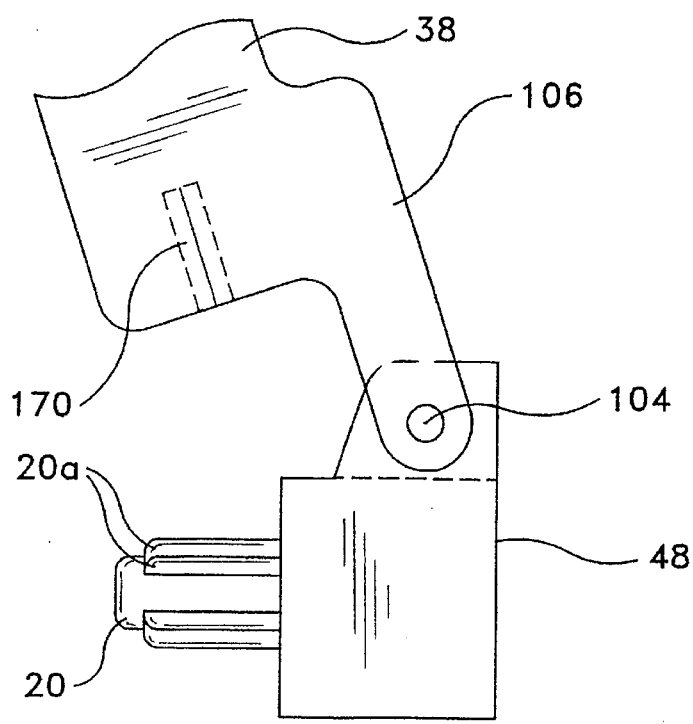
FIGS. 29–31 depict one embodiment for effecting repeated secure but releasable closure of the shield of the present invention, FIG. 31 being a cross-section taken along line 31—31 of FIG. 30.
Figure 30:
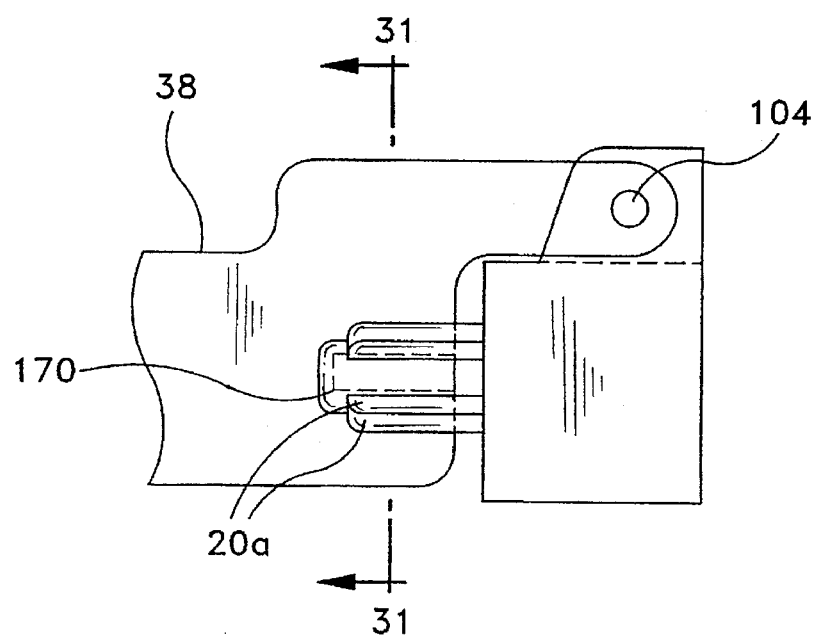
Figure 31:
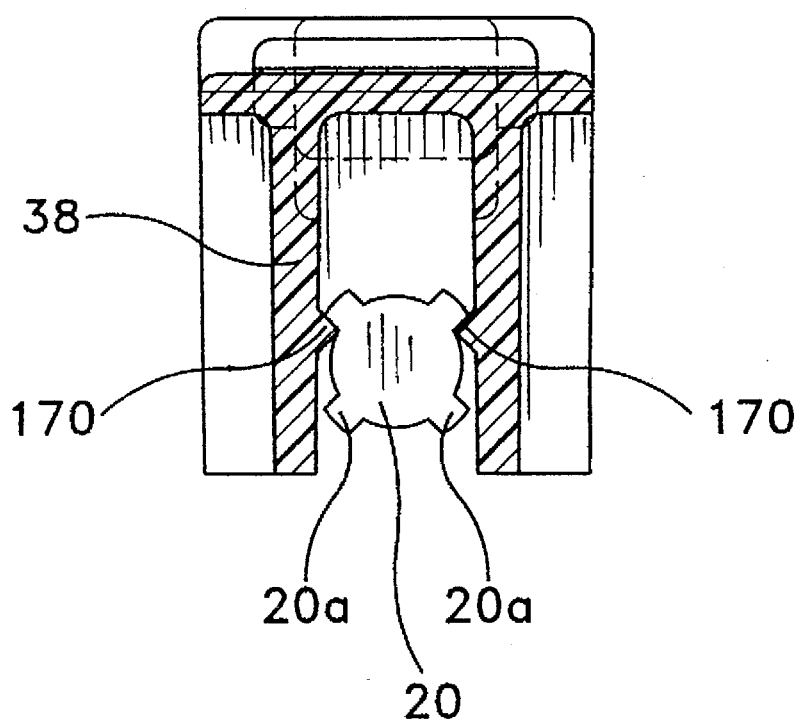

Thus, as seen in FIGS. 29 through 31, one way to effect repeated secure but releasable closing of the shield 38 vis-à-vis the piercing element 14 is to form a pair of rib elements 170 longitudinally aligned with the sheath 38 which are engageable with the individual riblets 20a associated with hub 20 of the piercing element. As here depicted, the rib elements 170 are formed on an interior portion of sheath 38. When the shield is rotated into its closed position, rib elements 170 are thrust into engagement beneath riblets 20a (as best seen in FIG. 31) so as to securely keep the shield 38 in a closed position. However, the shield 38 is releasable by a user upon an opening force exerted upon the shield. Note that with this embodiment, the user is given both tactile and audible indication of secure latching of sheath 38 with respect to hub 20, a useful feature when, for instance, the exigencies of the operating situation dictate rapid use of the product.

Figure 32:
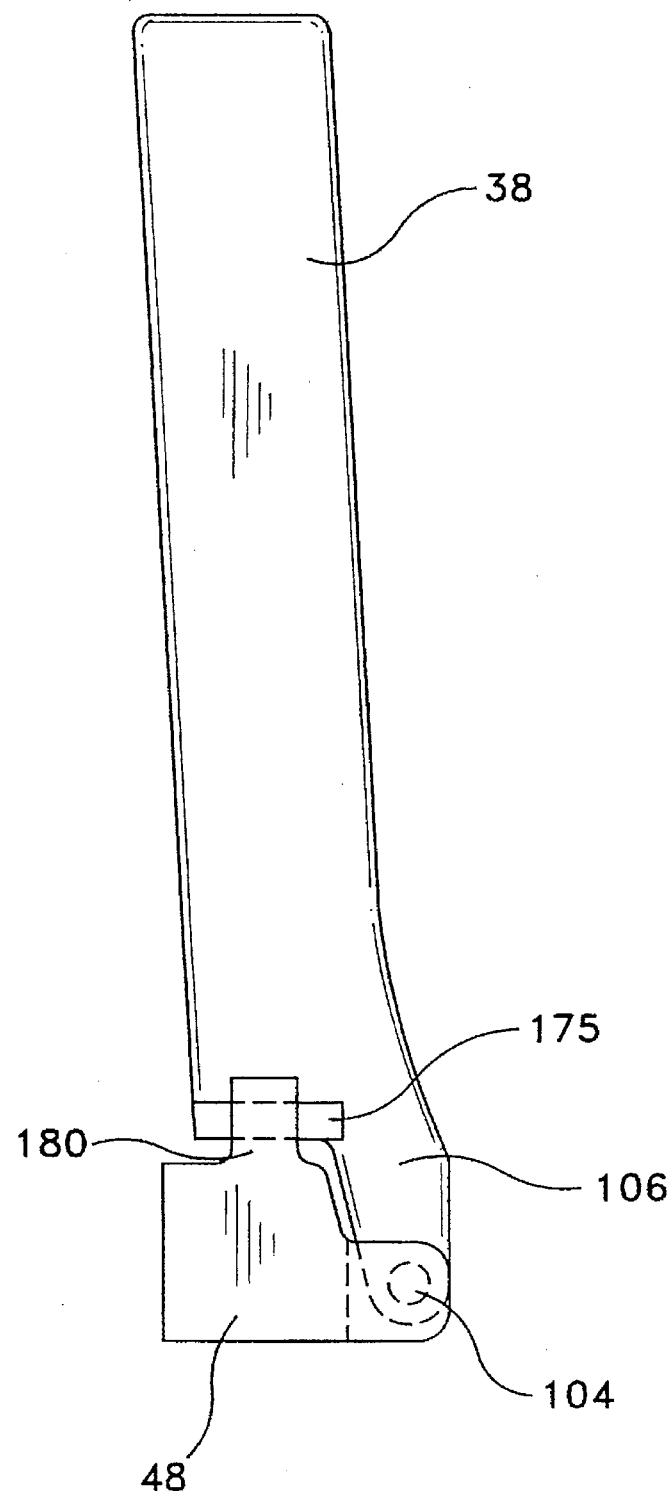
FIGS. 32–33 depict an alternate embodiment for effecting repeated secure but releasable closure of the shield of the present invention.
Figure 33:
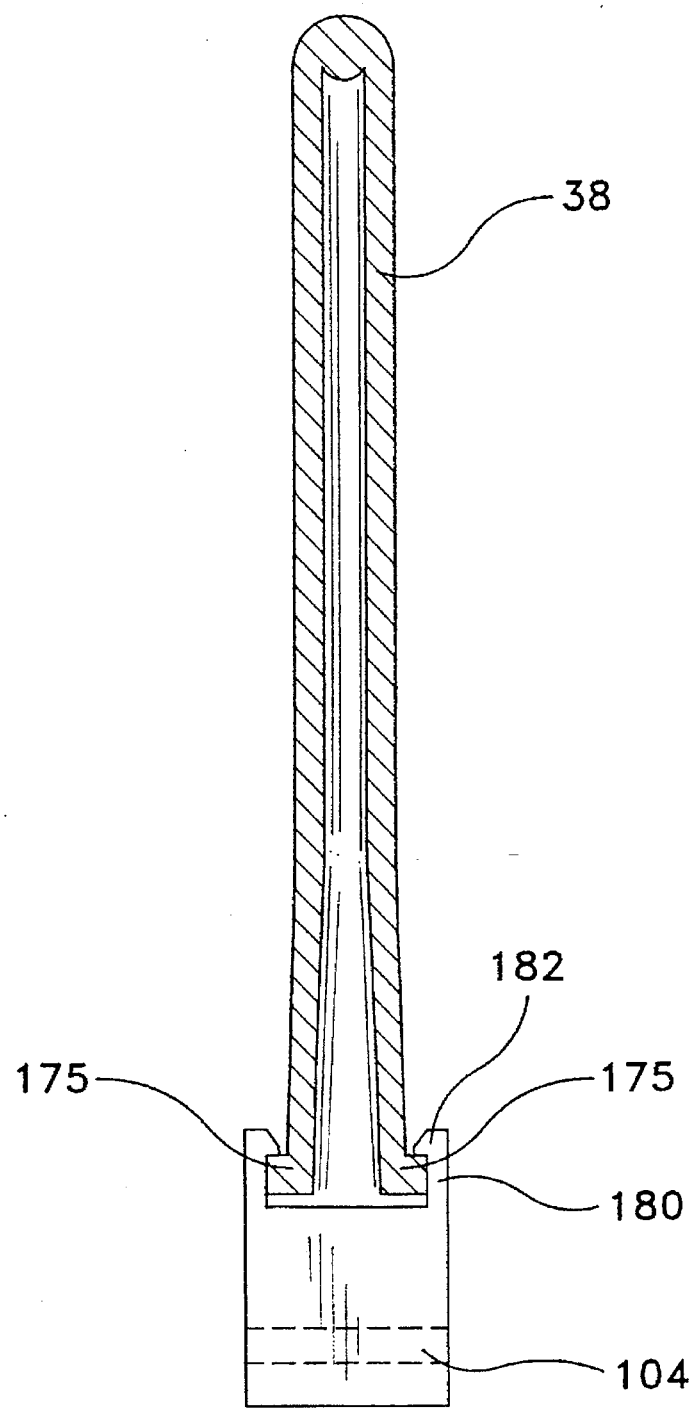

FIGS. 32–33 depict yet another embodiment for secure repeated but releasable closing of the shield 38 with respect to the piercing element 14. Here, a pair of ribs 175 is formed external to the sheath substantially perpendicular to the longitudinal axis of sheath 38. Mounting portion 48 includes a pair of engaging arms 180 on opposite sides of shield 38, with head portions 182 formed substantially perpendicular to the engaging arms 180. When the shield is rotated into position, ribs 175 are frictionally engaged by engaging arms 180 and their head portions 182 so as to frictionally, securely keep the shield 38 in its closed position. As before, audible and tactile indication of secure closing is given a user as further indication that the sheath is in its closed, secure position.

Figure 34:
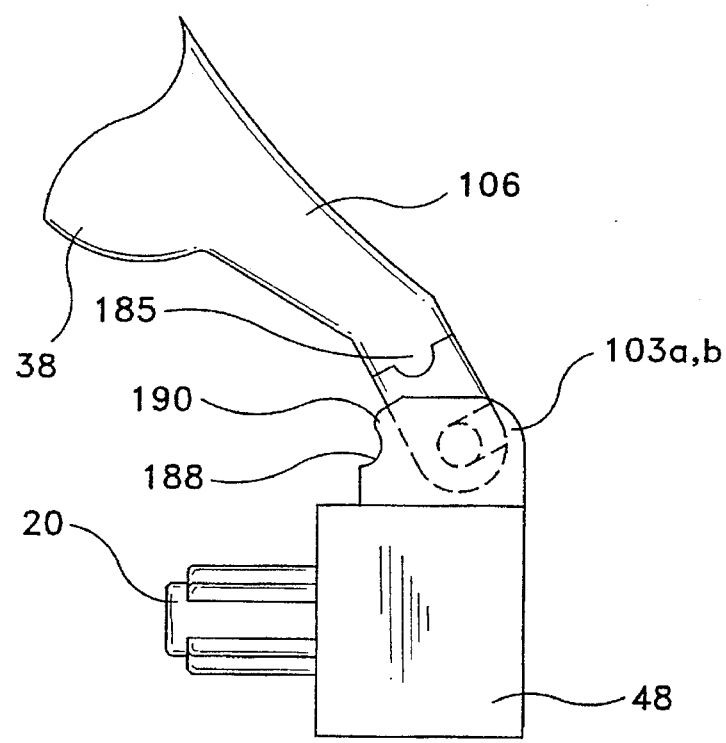
FIGS. 34–35 depict yet another alternative embodiment for effecting repeated secure but releasable closure of the shield of the present invention.
Figure 35:
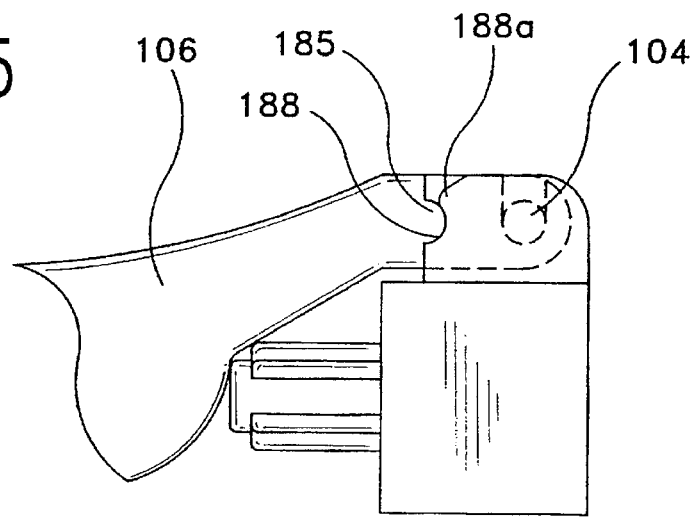

FIGS. 34 and 35 depict yet another embodiment for secure repeated but releasable closing of the shield 38 respective of the piercing element 14. Here, a pair of rounded pin elements 185 are formed on opposite sides of the arm 106, which pin elements are engageable in cutout openings 188 formed on either or both of side plates 103a, b. As before, the positioning of the pins 185 and the cutout openings 188 can be reversed. Each of the rounded cut-out openings 188 is preceded by a sloping wall portion 190 which assists in the transition of the pins 185 as the shield 38 is rotated into its closed position. The engagement between the pins 185 and the rounded openings 188 serve to keep shield 38 in its secure closed but releasable position. However, note that by forming cutout openings 188 with a bit of a overhang 188a above the pins 185, the shield 38 is prevented from inadvertent release unless intentional force is applied by the user. As with the prior two embodiments, audible and tactile indication of secure closing and release is provided to the user.

Moreover, as previously explained, flange 200 or tab 202 may be provided to enable a user to apply manual force to open or close the shield respective of the piercing element 14. FIGS. 36a–c, FIGS. 37a–c and FIGS. 38a–c depict, respectfully, various modifications of elements which enable precise, efficient, and easy digital manipulation of the shield so as to enable operation of the device.

Figure 36A:
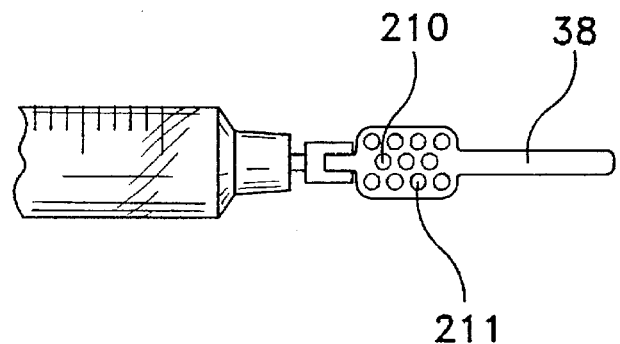
FIGS. 36a–36c depict one way to structure the shield of the present invention for ease of manipulation by a user.
Figure 36B:
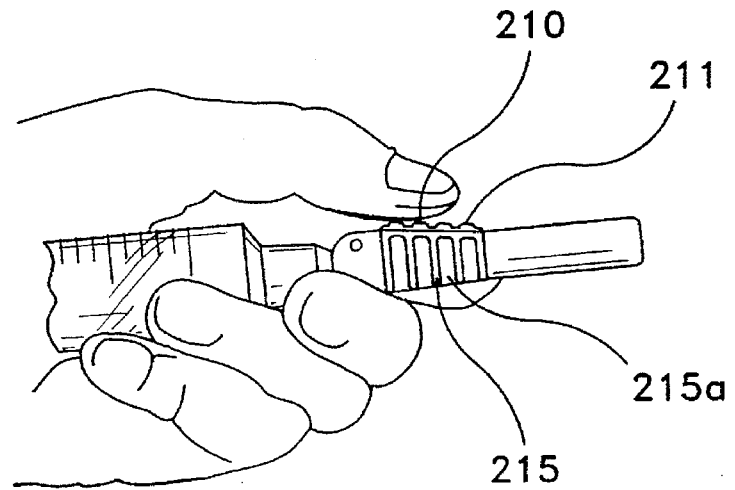
Figure 36C:
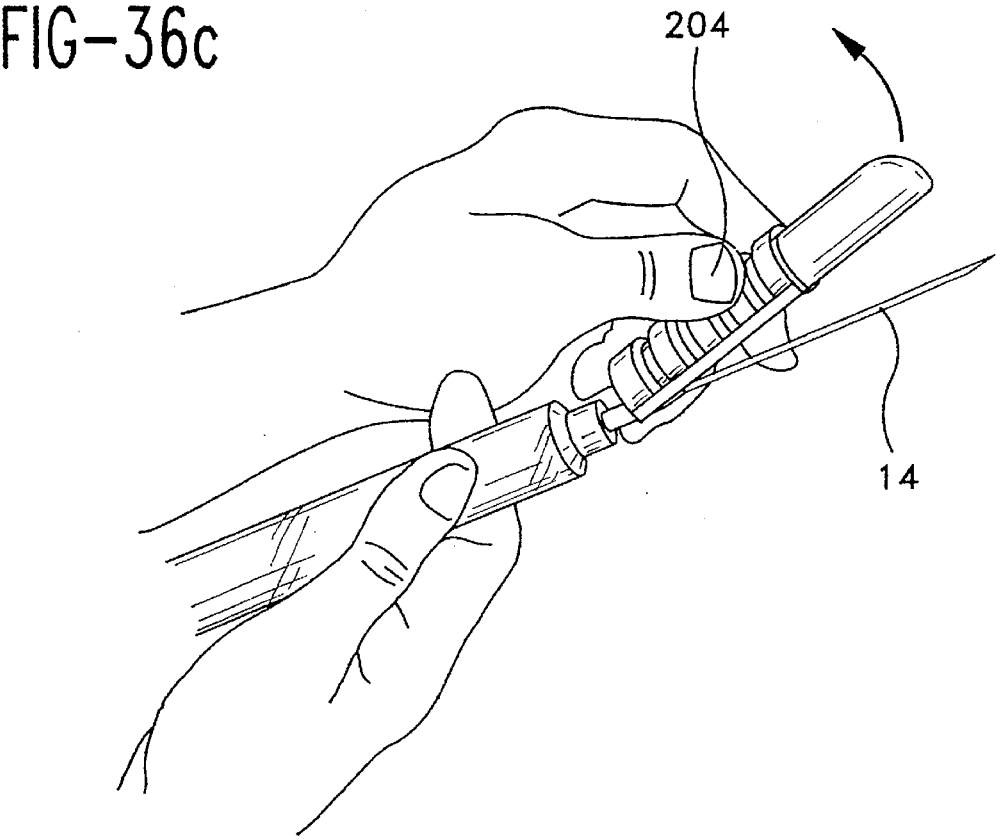

Turning more particularly to FIGS. 36a–c, here shield 38 is provided with a top-most gripping pad 210 having a plurality of tactile bumps 211 formed thereon. The sides of the shield 38 include ribbed surfaces 215 formed of a plurality of ribs 215a. A user 204 may grasp the fibbed surfaces 215 from either side of the shield 38 to conveniently actuate opening of the shield 38 respective of the piercing element 14. The grip pad 210, aided by tactile bumps 211, facilitate a user's thumb actuated closing of the shield 38 when desired.

Figure 37A:
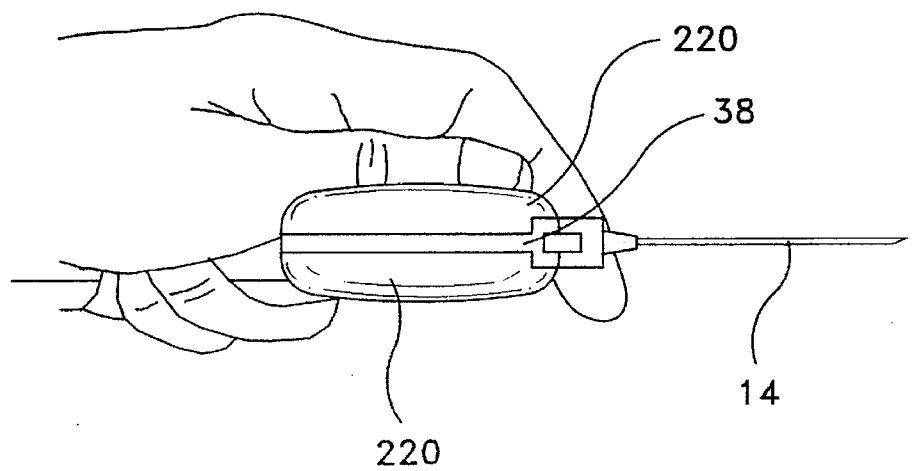
FIGS. 37a–37c depict another way to structure the shield of the present invention for ease of manipulation by a user.
Figure 37B:
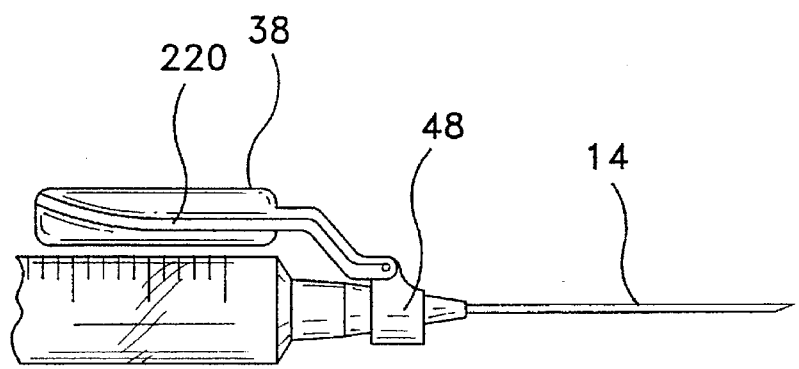
Figure 37C:
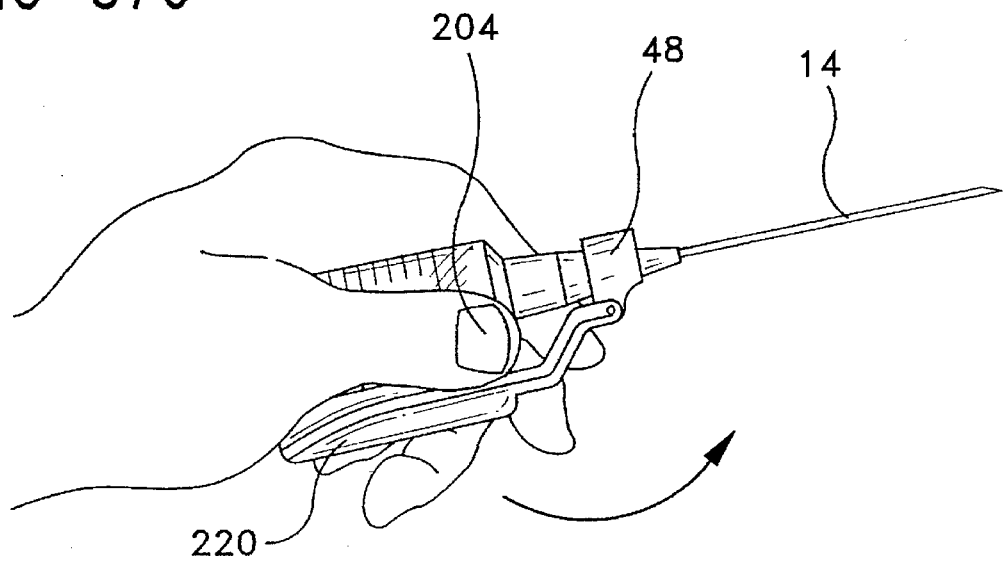

FIGS. 37a–c depict an embodiment of the shield 38 employing an ergonomically contoured fender 220 formed on either side of the shield 38. This design facilitates substantial one-handed actuation of the shield 38. A user is able to manipulate shield 38 with the same hand that holds the medical delivery device. With this design, a user's fingers 204 remain behind the fender 220, providing an added measure of security in that the user's fingers 204 do not substantially approach the piercing element 14. By providing an ergonomically contoured shape to the fenders 220, the natural motion of a user's thumb 204 cooperates with the curved design of the fenders 220 to enable safe, automatic closing of the shield 38 respective of the piercing element 14.

Figure 38A:
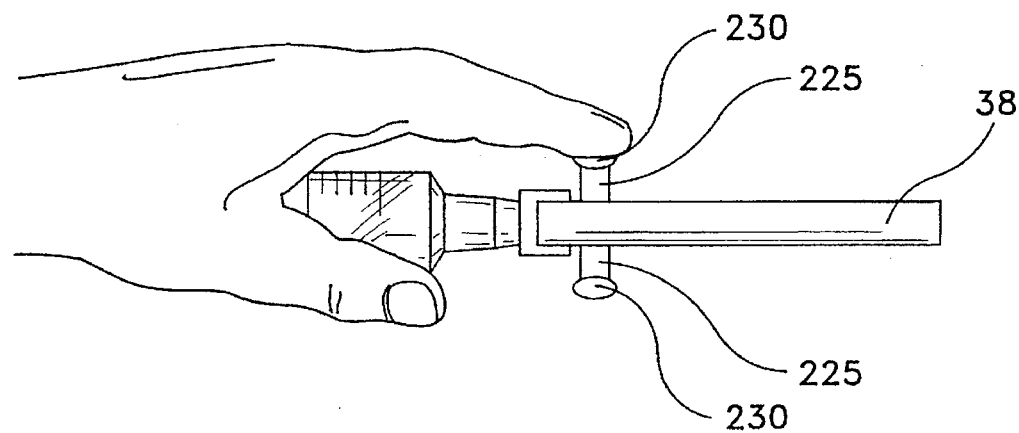
FIGS. 38a–38c depict another way to structure the shield of the present invention for ease of manipulation by a user.
Figure 38B:
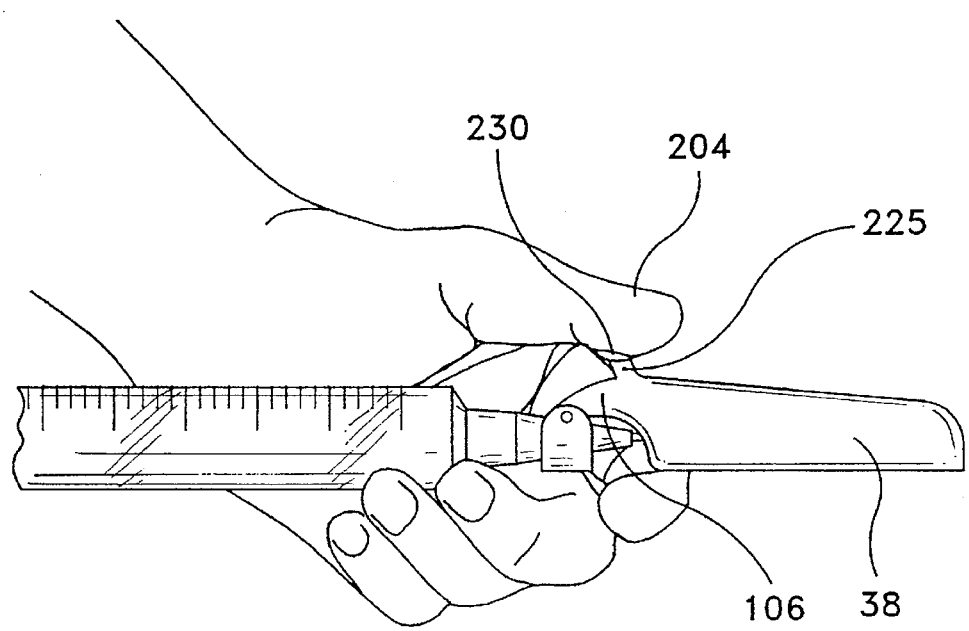
Figure 38C:
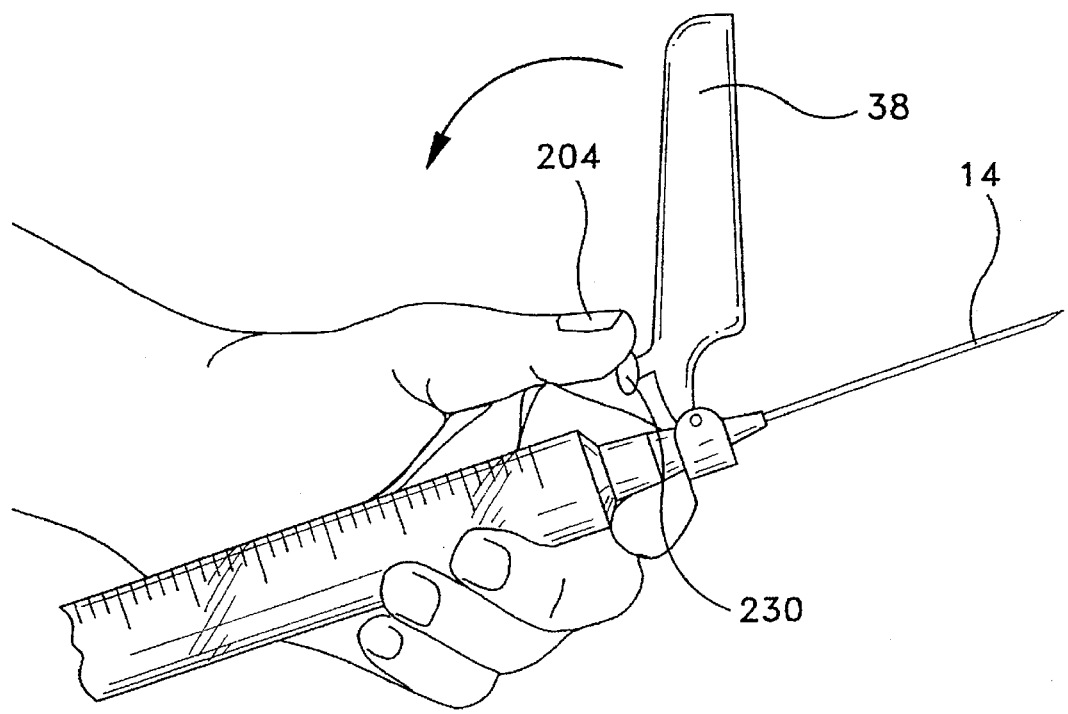

FIGS. 38a–c depict yet another embodiment for ergonomic actuation of the shield 38 respective of the piercing element 14. Here, a pair of stub links 225 is formed on either side of shield 38 and preferably at an upper portion of shield 38 adjacent the arm portion 106. The tips of each of these stub links 225 includes a rounded ball portion 230 which is engageable with the fingers 204 of a user. An advantage of this design is that the ball portions 230 are operable from either the side of the shield 38 or on top of the shield 38, enabling safe distance between a user's fingers 204 in either of the dosing or opening operations. For instance, when opening of the shield 38 is desired, a user's fingers 204 may engage the ball 230 from the side of the shield 38, so as to stay away from the piercing element. However, when it is desired to close the shield 38, a user's fingers 204 may approach ball portions 230 behind the shield 38 and the piercing element 14, so that the user's fingers 204 are always protected from the piercing element 14.

It will be appreciated and understood by those skilled in the art that further and additional forms of the invention may be devised without departing from the spirit and scope of the appended claims, the invention not being limited to the specific embodiments shown.

We claim:

1. A protective barrier assembly for a piercing element, comprising:

an elongate piercing element having a distal end and a proximal end; and a barrier element for selectively averting touch contact with said piercing element, said barrier element including an elongate channel portion dimensioned to receive said elongate piercing element, a collar secured adjacent the proximal end of the piercing element, and an arm having one end affixed to said channel portion and having a second end pivotably affixed to said collar, said barrier element pivotable between a first portion, wherein the distal end of said piercing element is exposed, and a second position, wherein the distal end of said piercing element is substantially enclosed within the channel portion to protectively cover the distal end of the piercing element, said arm including a retaining means for lockingly engaging with said collar to secure said barrier element in said second position.

2. The protective barrier assembly of claim 1, wherein said piercing element comprises a hub component at said proximal end, said hub component adapted to communicate with a medical delivery device.

3. The protective barrier assembly of claim 1, wherein said collar member is rotatably affixed to said piercing element.

4. The protective barrier assembly of claim 1, wherein said retaining means comprises a pin member and an opening is formed in said collar adjacent the proximal end of the piercing element, said pin member adapted to be lockingly engaged in said opening.

5. The protective barrier assembly of claim 1, wherein said piercing element is a needle cannula.

6. A protective barrier assembly for a piercing element, comprising:

a relatively elongate piercing element having a distal end and a proximal end;

a barrier element for selectively averting touch contact with said piercing element, said barrier element comprising a collar portion secured adjacent the proximal end of the piercing element, a relatively elongate channel portion configured to enclose the piercing element, and an arm having one end affixed to said channel portion and having a second end pivotably secured to the collar portion, said channel portion pivotable between a first position wherein the distal end of said piercing element is uncovered and a second position wherein the distal end of the piercing element is protectively covered; said arm including a retaining means for engaging said collar portion upon pivoting said channel portion to said second position for retaining said channel portion in said second position.

7. The protective barrier assembly of claim 6, wherein said retaining means lockingly engages said channel portion in said second position upon pivoting said channel portion to said second position.

8. The protective barrier assembly of claim 7, wherein said retaining means comprises:

a pin having a compressible head portion having a first width, the pin fixed to said channel portion; and said collar portion defining a hole having a second width narrower than the first width of the compressible head portion, wherein said compressible head portion is urged through said hole when the channel portion is pivoted into the second position to lock the channel portion in said second position.

9. The protective barrier assembly of claim 7, wherein said retaining means comprises:

a latch fixed to said arm and a protrusion fixed on said collar portion, said latch urged beneath said protrusion when the channel portion is pivoted into said second position to lock said channel portion in said second position.

10. The protective barrier assembly of claim 7, wherein said retaining means comprises:

a pin having a pair of edges defining a first width, said pin fixed to said arm; and said collar portion defining an orifice for accepting said pin, said orifice having a receptacle end defining an opening having a second width narrower than the first width of the pin, wherein the pin is compressed through the opening and urged into the receptacle when the channel portion is pivoted into the second position to lock the channel portion in said second position.

11. The protective barrier assembly of claim 6, wherein said channel portion is pivotable to a closed position intermediate said first and second positions, the distal end of said piercing element protectively enclosed by said channel portion in said closed position, wherein said retaining means is configured to releasably retain said channel portion in said closed position, and wherein said retaining means is configured to lockingly secure said channel portion in said second position.

12. The protective barrier assembly of claim 11, wherein said retaining means comprises:

a latch fixed to said arm and a protrusion fixed on said collar portion; and a pin having a first diameter fixed to said arm and an orifice defined on said collar portion, said orifice having a neck portion with a second diameter less than the first diameter of the pin and an opening with a third diameter configured to accommodate the pin therein, wherein upon pivoting of said channel portion to said closed position said pin will be engaged in said neck portion to releasably retain said channel portion in said closed position, and upon further pivoting of said channel portion to said second position, said latch will be urged into locking engagement with said protrusion to lock the channel portion in said second position.

13. The protective barrier assembly of claim 11, wherein said retaining means comprises:

a latch fixed to said arm and a protrusion fixed to said collar portion; and said arm comprising at least one protrusion releasably engageable with a detent fixed to said collar portion, wherein upon pivoting of said channel portion to said closed position said channel protrusion is engaged with said collar detent to releasably retain said channel portion in said closed position, and upon further pivoting of said channel portion to said second position, said latch will be urged into locking engagement with said collar protrusion to lock the channel portion in said second position.

14. The protective barrier assembly of claim 11, wherein said retaining means comprises:

said arm portion including at least one engagement edge and at least one locking edge, said collar portion including at least one detent releasably engageable with the engagement edge of the arm and said collar portion further including a locking portion adapted to lockingly retain said locking edge, wherein upon pivoting of said channel portion to said closed position, said engagement edge of said arm is engaged with said collar detent to maintain said channel portion in said closed position, and upon further pivoting of said channel portion to said second position, said locking edge of the arm will be thrust into said locking portion of said collar portion to lock the channel portion in said second position.

* * * * *